(12) United States Patent
Quave et al.

(10) Patent No.: US 12,083,132 B1
(45) Date of Patent: Sep. 10, 2024

(54) BOTANICAL EXTRACTS AND COMPOUNDS FROM SCHINUS PLANTS AND METHODS OF USE

(71) Applicant: Emory University, Atlanta, GA (US)

(72) Inventors: Cassandra L. Quave, Atlanta, GA (US); James Lyles, Sandy Springs, GA (US); Gina Porras-Brenes, Atlanta, GA (US); Huaqiao Tang, Atlanta, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 0 days.

(21) Appl. No.: 18/121,280

(22) Filed: Mar. 14, 2023

Related U.S. Application Data

(63) Continuation of application No. 17/357,353, filed on Jun. 24, 2021, now Pat. No. 11,633,407, which is a continuation of application No. 16/290,543, filed on Mar. 1, 2019, now Pat. No. 11,065,261, which is a continuation-in-part of application No. 15/205,493, filed on Jul. 8, 2016, now Pat. No. 10,675,315.

(60) Provisional application No. 62/190,802, filed on Jul. 10, 2015.

(51) Int. Cl.
| | | |
|---|---|---|
| *A61K 31/569* | (2006.01) | |
| *A61K 9/00* | (2006.01) | |
| *A61K 31/575* | (2006.01) | |
| *A61K 36/22* | (2006.01) | |
| *A61K 45/06* | (2006.01) | |
| *A61P 31/04* | (2006.01) | |

(52) U.S. Cl.
CPC ............ *A61K 31/575* (2013.01); *A61P 31/04* (2018.01)

(58) Field of Classification Search
CPC .. A61K 31/569; A61K 2300/00; A61K 36/22; A61K 45/06; A61K 9/0014
See application file for complete search history.

(56) References Cited

PUBLICATIONS

Assimopoulou AN, et al. "GC-MS analysis of penta- and tetra-cyclic triterpenes from resins of *Pistacia* species. Part I. *Pistacia lentiscus* var. Chia",. Biomed. Chromatogr.,19: 285-311; doi: 10.1002/bmc.454. (Year: 2005).*

* cited by examiner

*Primary Examiner* — Aaron J Kosar
(74) *Attorney, Agent, or Firm* — Kilpatrick Townsend & Stockton LLP

(57) ABSTRACT

This disclosure relates to extracts from the Anacardiaceae (cashew plant family) and compositions comprising compounds contained therein. In certain embodiments, the extracts are derived from the fruit of a *Schinus* plant. In certain embodiments, the disclosure relates to methods of treating or preventing bacterial infections, acne, and other related uses.

18 Claims, 21 Drawing Sheets

| Peak # | RT (min) | (%) Relative Abundance | | Formula (Δ- ppm)[a] |
|---|---|---|---|---|
| | | Neg. Mode | Pos. Mode | |
| 1 | 39.78 | 0.00 | 0.55 | $C_{54}H_{59}O_6$ (1.3) |
| 2 | 45.70 | 11.65 | 3.59 | $C_{30}H_{17}O_{10}$ (0.2) |
| 3 | 46.28 | 8.39 | 2.14 | $C_{30}H_{17}O_{10}$ (0.2) |
| 4 | 47.25 | 22.13 | 3.37 | $C_{30}H_{21}O_{10}$ (1.4) |
| 5 | 47.79 | 3.03 | 0.62 | $C_{30}H_{21}O_{10}$ (-0.2) |
| 6 | 48.19 | 4.66 | 0.73 | $C_{53}H_{95}O_{15}$ (-1.3) |
| 7 | 49.49 | 1.14 | 0 | $C_{31}H_{45}O_7$ (-0.6) |
| 8 | 51.12 | 0.53 | 0.93 | $C_{45}H_{66}O_{15}$ (-0.3) |
| 9 | 51.43 | 0.27 | 0.54 | $C_{29}H_{37}O_3$ (3.7) |
| 10 | 52.01 | 3.5 | 0.43 | $C_{30}H_{45}O_6$ (0.5) |
| 11 | 53.10 | 0 | 0.31 | $C_{48}H_{70}O_3$ (-9.6) |
| 12 | 53.53 | 0.98 | 1.31 | $C_{40}H_{69}O_8$ (0.9) |
| 13 | 54.48 | 0 | 2.11 | $C_{40}H_{69}O_8$ (2.5) |
| 14 | 55.01 | 5.33 | 2.33 | $C_{30}H_{45}O_4$ (0.9) |
| 15 | 55.44 | 2.14 | 2.33 | $C_{30}H_{45}O_4$ (2.9) |
| 16 | 56.12 | 0.63 | 1.78 | $C_{40}H_{61}O_6$ (0.9) |
| 17 | 56.58 | 7.99 | 8.52 | $C_{30}H_{45}O_4$ (1.0) |
| 18 | 57.76 | 1.52 | 2.86 | $C_{30}H_{47}O_4$ (3.1) |
| 19 | 58.06 | 1.05 | 2.09 | $C_{30}H_{45}O_4$ (3.4) |
| 20 | 58.32 | 1.09 | 2.77 | $C_{53}H_{97}O_{13}$ (2.1) |
| 21 | 58.48 | 2.07 | 0 | $C_{30}H_{45}O_6$ (0.1) |
| 22 | 58.74 | 3.49 | 10.4 | $C_{30}H_{45}O_4$ (2.2) |
| 23 | 59.35 | 2.39 | 3.43 | $C_{30}H_{47}O_4$ (1.9) |
| 24 | 59.73 | 5.37 | 4.12 | $C_{30}H_{45}O_5$ (2.1) |
| 25 | 60.44 | 2.06 | 2.55 | $C_{30}H_{45}O_4$ (0.1) |
| 26 | 60.75 | 1.23 | 1.48 | $C_{30}H_{45}O_4$ (0.8) |
| 27 | 61.72 | 1.56 | 2.29 | $C_{30}H_{47}O_5$ (1.5) |

FIG. 8B

| Peak | Formula (Δ- ppm)[a] | Putative Compounds | ESI | m/z[b] | $MS^2$ |
|---|---|---|---|---|---|
| 1 | $C_{54}H_{59}O_6$ (1.3) | no matches | + | 391.2296, 413.2114, 803.4316 | ND |
| 2 | $C_{30}H_{17}O_{10}$ (0.2) | amentoflavone; agathisflavone; robustaflavone | - | 537.0828 | 375.1374, 443.1003 |
| 3 | $C_{30}H_{17}O_{10}$ (0.2) | see peak 1 | - | 537.0826 | 375.1590, 443.1464 |
| 4 | $C_{30}H_{21}O_{10}$ (1.4) | chamaejasmin; tetrahydroamentoflavone; tetrahydrorobustaflavone | - | 541.1147, 1083.2380 | 389.1906, 415.1563 |
| 5 | $C_{30}H_{21}O_{10}$ (-0.2) | see peak 3 | - | 541.1138 | 389.1694, 415.1370 |
| 6 | $C_{53}H_{95}O_{15}$ (-1.3) | no matches | - | 485.3277, 531.3344, 971.6664 | 941.8088, 951.2601, 971.7518 |
| 7 | $C_{31}H_{45}O_7$ (-0.6) | no matches | - | 529.3167 | 485.5292 |
| 8 | $C_{45}H_{66}O_{15}$ (-0.3) | no matches | + | 415.2112, 432.2376, 493.2250, 846.4404 | ND |
| 9 | $C_{29}H_{37}O_3$ (3.7) | no matches | - | 433.2764, 455.2583 | 400.9561, 415.3339 |
| 10 | $C_{30}H_{45}O_6$ (0.5) | no matches | - | 501.3224 | 439.3959 |
| 11 | $C_{48}H_{70}O_3$ (-9.6) | no matches | + | 356.2793, 694.5253 | 542.3829, 676.2984 |
| 12 | $C_{40}H_{69}O_8$ (0.9) | no matches | + | 356.2795, 377.2299, 677.4993, 699.4816 | 557.3066, 647.4799 |
| 13 | $C_{40}H_{69}O_8$ (2.5) | no matches | + | 677.5004, 699.4831 | 525.4104, 5557.4151, 647.5023 |

FIG. 8C

| | | | | | |
|---|---|---|---|---|---|
| 14 | C$_{30}$H$_{45}$O$_4$ (0.9) | albsapogenin; (3α,13α,14β, 17α,20S,24Z)-3-hydroxy-21-oxo-lanosta-8,24-dien-26-oic acid; (13α,14β,17α,20R,24Z)-3α-hydroxy-21-oxolanosta-8,24-dien-26-oic acid; (3α, 13α,14β,17α,24Z)-3-hydroxy-7-oxo-lanosta-8,24-dien-26-oic acid; mollinoic acid | - | 469.3327, 515.3390, 939.6748 | 351.3897, 451.4088 |
| 15 | C$_{30}$H$_{45}$O$_4$ (2.9) | see peak 13 | - | 469.3336, 515.3379 | ND |
| 16 | C$_{40}$H$_{61}$O$_6$ (0.9) | no matches | - | 533.3491, 637.4479, 683.4534 | 607.5950 |
| 17 | C$_{30}$H$_{45}$O$_4$ (1.0) | see peak 13 | - | 469.3328, 515.3391, 939.6760 | 407.4528 |
| 18 | C$_{30}$H$_{47}$O$_4$ (3.1) | see peak 13 | + | 471.3483 | 453.4008 |
| 19 | C$_{30}$H$_{45}$O$_4$ (3.4) | isomasticadienonalic acid | + | 469.3328 | 260.1903, 332.2413, 452.3980 |
| 20 | C$_{53}$H$_{97}$O$_{13}$ (2.1) | no matches | + | 471.3485, 621.4551, 941.6944 | 941.6543 |
| 21 | C$_{30}$H$_{45}$O$_6$ (0.1) | no matches | - | 501.322 | 439.3777 |
| 22 | C$_{30}$H$_{45}$O$_4$ (2.2) | see peak 13 | - | 469.3333, 515.3384, 939.6736 | 439.4702 |
| 23 | C$_{30}$H$_{47}$O$_4$ (1.9) | see peak 13 | + | 471.3488 | 217.1912, 435.3044, 453.3376 |
| 24 | C$_{30}$H$_{45}$O$_5$ (2.1) | no matches | - | 485.3282, 531.3338, 971.6649 | 453.3968, 467.3944 |
| 25 | C$_{30}$H$_{45}$O$_4$ (0.1) | see peak 13 | - | 469.3323, 515.3383, 939.6758 | 451.3724 |
| 26 | C$_{30}$H$_{45}$O$_4$ (0.8) | see peak 13 | - | 469.3327, 515.3375 | 451.3639 |
| 27 | C$_{30}$H$_{47}$O$_5$ (1.5) | no matches | - | 487.3436, 533.3478, 975.6950 | 455.4224, 469.4080 |

FIG. 8D

BOTANICAL EXTRACTS AND COMPOUNDS FROM SCHINUS PLANTS AND METHODS OF USE

CROSS-REFERENCE TO RELATED APPLICATIONS

This application is a continuation of U.S. application Ser. No. 17/357,353 filed Jun. 24, 2021, now pending, which is a continuation of U.S. application Ser. No. 16/290,543 filed Mar. 1, 2019, now issued as U.S. Pat. No. 11,065,261 on Jul. 20, 2021, which is a continuation-in-part of U.S. application Ser. No. 15/205,493 filed Jul. 8, 2016, now issued as U.S. Pat. No. 10,675,315 on Jun. 9, 2020, which claims priority to U.S. Provisional Application No. 62/190,802 filed Jul. 10, 2015. The entirety of each of these applications is hereby incorporated by reference for all purposes.

STATEMENT REGARDING FEDERALLY FUNDED RESEARCH

This invention was made with government support under R01AT007052 awarded by the National Institutes of Health. The government has certain rights in the invention.

BACKGROUND

Since the widespread introduction of antibiotics in the 1940s, the same storyline has repeated itself over and over again: new antibiotic is introduced and then resistant variants emerge and quickly spread, effectively limiting the utility and lifespan of the drug. Staphylococci are frequently the cause of hospital infections such as infections from implanted medical devices. Many staphylococcal strains have become resistant to many modern day antibiotics. Improved therapies are needed.

One proposed strategy to overcome the problem of highly virulent and resistant variants is to indirectly attack bacteria by interfering with their means of communication, also known as quorum sensing. Targeting microbial communication makes sense because bacteria coordinate many of their virulence and pathogenesis pathways through these systems. Quave et al., report quorum sensing inhibitors of *Staphylococcus aureus* from botanical extracts. Planta Med. 2011, 77(02): 188-95. See also Quave & Horswill, Front Microbiol, 2014, 5:706.

*Schinus terebinthifolia* Raddi (synonym: *Schinus terebinthfolius*) is a flowering plant in the family Anacardiaceae, which can be found in Brazil, the Caribbean and across the southern United States. It is considered an invasive species in a number of countries. El-Massry et al. report chemical compositions and antioxidant/antimicrobial activities of various samples prepared from *Schinus terebinthifolia* leaves cultivated in Egypt. J Agric Food Chem, 2009, 57:5265-5270. Moura-Costa et al. report antimicrobial activity of plants used as medicinals on an indigenous reserve in Rio das Cobras, Parana, Brazil. J Ethnopharmacol, 2012, 143:631-638. Melo et al. report alcohol extract of *Schinu sterebinthifolia* Raddi (Aanacardiaceae) as a local antimicrobial agent in severe autogenously fecal peritonitis in rats. Acta cirurgica brasileira/Sociedade Brasileira para Desenvolvimento Pesquisa em Cirurgia, 2014, 29 Suppl 1:52-56. See also Martius, Systema de Materia *Medica* Vegetal Brasileira. Rio de Janeiro, 1854; Moreira, Diccionario de Plantas Medicinaes Brasileiras. Rio de Janeiro, 1862; Chernoviz, Formulario ou Guia *Medica*. 6 ed. Paris, 1864; Burton, Viagens aos planaltos do Brasil—Tomo I: Do Rio de Janeiro a Morro Velho, 1868.

References cited herein are not an admission of prior art.

SUMMARY

This disclosure relates to extracts from the cashew family of plants (Anacardiaceae) and compositions comprising one or more compounds contained therein and related uses reported herein. In certain embodiments, the extracts are derived from the fruit of a *Schinus* plant such as *Schinus terebinthifolia*.

In certain embodiments, the disclosure relates to extracts comprising a fruit derived mixture of compounds from a *Schinus* plant wherein the extracting process comprises one or more of the following steps of: mixing a fruit with an alcohol, e.g., ethanol, methanol, or aqueous mixtures thereof (ethanol:water or methanol:water, 50-95% alcohol, 80% methanol) under conditions such that fruit compounds dissolves in the methanol and removing the methanol providing a methanol derived mixture of compounds; partitioning the methanol derived mixture of compounds between hexane and water providing a water derived mixture of compounds; partitioning the water derived mixture of compounds between ethyl acetate and water providing a second water derived mixture of compounds; partitioning the second water derived mixture of compounds by mixing the second water derived mixture of compounds with n-butanol under conditions such that fruit compounds dissolve in the n-butanol and removing the n-butanol providing an n-butanol derived mixture of compounds; and purifying the n-butanol derived mixture of compounds by liquid chromatography.

In certain embodiments, the extract comprises a mixture of compounds having at least one component from each of the following groups a) to d): a) a compound having a molecular formula of $C_{30}H_{17}O_{10}$; b) a compound having a molecular formula of $C_{30}H_{21}O_{10}$; c) a compound having a molecular formula of $C_{30}H_{45}O_4$; and d) a compound having a molecular formula of $C_{30}H_{45}O_4$.

In certain embodiments, this disclosure relates to methods of treating or preventing bacterial infections or acne comprising administering to a subject in need thereof or contacting the skin of a subject in need thereof with a formula comprising an extract or one or more compounds in an extract as disclosed herein. In certain embodiments, the formula is administered in combination with another antibiotic.

In certain embodiments, this disclosure relates to methods of treating or preventing a toxin-mediated bacterial infection comprising administering an effective amount of an *Schinus* extract or compounds contained therein to a subject in need thereof, including a subject at risk of, exhibiting symptoms of, or diagnosed with a staphylococcal scalded skin syndrome (esp. in neonates), abscesses, necrotizing fasciitis, sepsis, or atopic dermatitis (eczema).

In certain embodiments, the subject is at risk of, exhibiting symptoms of, or diagnosed with toxic shock syndrome, scalded skin syndrome, abscesses, furuncles, cellulitis, folliculitis, bloodstream infections, medical device infections, pneumonia, osteomyelitis, staphylococcal food poisoning, skin and soft tissue infections, endocarditis, eczema, atopic dermatitis, psoriasis, impetigo, septic arthritis, brain abscess, burn wounds, venous ulcers, diabetic foot ulcers, surgical wounds, post-operation infections, carbuncles, meningitis, bacteremia, necrotizing pneumonia, or necrotizing fasciitis.

In certain embodiments, the disclosure contemplates the use of an extract or one or more compounds in an extract disclosed herein in a tampon for the treatment or prevention of toxic shock syndrome.

In certain embodiments, the disclosure relates to a pharmaceutical or cosmetic formulation comprising an extract or one or more compounds in an extract disclosed herein and a pharmaceutically acceptable excipient or cosmetically acceptable excipient. In certain embodiments, the disclosure relates to a liquid or gel formulation optionally further comprising an antibacterial agent, a topical steroid, an anti-inflammatory agent, a promoter of skin barrier function, a skin moisturizer or combinations thereof. In certain embodiments the antibacterial agent is daptomycin, linezolid, vancomycin, nafcillin, cefazolin, dicloxacillin, clindamycin, rifampin, sulfamethoxazole-trimethoprim (Bactrim), or botanical antibacterial agents, e.g., *Melaleuca alternifolia* (tea tree oil).

In certain embodiments, the compound is in the form of an aqueous solution further comprising a buffering agent, oil, phosphate buffer, sodium or potassium salt, a saccharide, polysaccharide, or solubilizing agent.

Uses as an injectable product (for intravenous, intramuscular, subcutaneous, intradermal injections, intraperitoneal, or other administration) are contemplated. In certain embodiments, the disclosure relates to a pharmaceutical injectable formulation comprising an extract or one or more compounds in an extract disclosed herein and a pharmaceutically acceptable excipient. In certain embodiments, the disclosure relates to an injectable formulation optionally further comprising an antibacterial agent, a topical steroid, an anti-inflammatory agent, or combinations thereof. In certain embodiments the antibacterial agent is daptomycin, linezolid, vancomycin, nafcillin, cefazolin, dicloxacillin, clindamycin, rifampin, sulfamethoxazole-trimethoprim (Bactrim), or botanical antibacterial agents, e.g., *Melaleuca alternifolia* (tea tree oil).

In certain embodiments, the disclosure relates to a pharmaceutical composition comprising an extract or one or more compounds in an extract disclosed herein formulated with an enteric coating.

In certain embodiments, the disclosure relates to a solid or liquid soap or lotion comprising an extract or one or more compounds in an extract disclosed herein and a fatty acid.

In certain embodiments, the disclosure relates to a medical device comprising a coating comprising an extract or one or more compounds in an extract disclosed herein.

In certain embodiments, the disclosure relates to a tampon or tampon fibers comprising an extract or one or more compounds in an extract disclosed herein and an absorbent material.

In certain embodiments, the disclosure relates to a wound dressings or wound rinse comprising an extract or one or more compounds in an extract disclosed herein wherein the wound dressing comprises an absorbent pad and optionally an adhesive.

In certain embodiments, the disclosure relates to disinfectant sprays or wipes formulation for surfaces and fomites, comprising an extract and one or one or more compounds in an extract disclosed herein wherein the spray or wipe comprises an extract or one or more compounds in an extract disclosed herein such as a formula including chlorine-based disinfectants.

In certain embodiment, this disclosure contemplates that compounds disclosed herein are used in a substantially purified form. For example, prior to addition to a pharmaceutical formulation the compounds may be purified to contain less than 50%, 40%, 30%, 20%, 10%, or 5%, by weight impurities or derivatives of the compound.

BRIEF DESCRIPTION OF THE DRAWINGS

FIG. 8B shows a table negative and positive ESI Mass spectrometry (m/z) analysis of 430D-F5 with calculated chemical formula corresponding HPLC-DAD chromatogram peaks reported in FIG. 8A.

FIG. 8C shows putative compounds based on ESI data for peaks 1-13 in Table 8B.

FIG. 8D shows putative compounds based on ESI data for peaks 14-27 in Table 8B.

DETAILED DESCRIPTION

Figure 1:
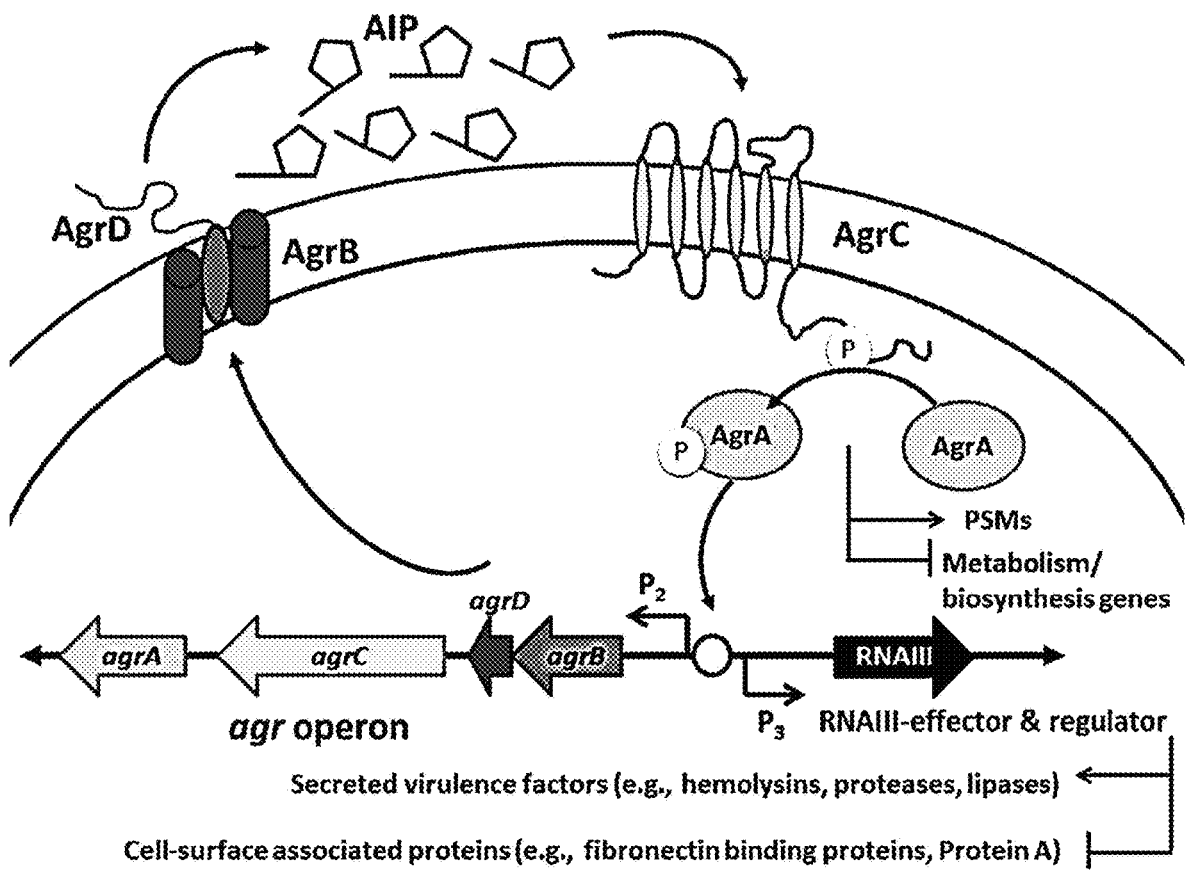
FIG. 1 illustrates the regulation of *S. aureus* pathogenesis with quorum sensing. *S. aureus* produces an extensive array of enzymes, hemolysins, and toxins that are essential to its ability to spread through tissues and cause disease. These virulence factors serve a wide scope of purposes in the infection process, including disruption of the epithelial barrier, inhibition of opsonization by antibody and complement, neutrophil cytolysis, interference with neutrophil chemotaxis, and inactivation of antimicrobial peptides. The expression of these invasive factors is controlled by cell-density quorum sensing using the autoinducing peptide (AIP) molecule. Like other quorum sensing signals, AIP accumulates outside the cell until it reaches a critical concentration and then binds to a surface receptor called AgrC, initiating a regulatory cascade. Since AIP controls the expression of accessory factors for *S. aureus*, this regulatory system has been named the accessory gene regulator (agr), and the majority of the proteins necessary for this quorum-sensing system to function are encoded in the agr chromosomal locus.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used herein, the term "combination with" when used to describe administration with an additional treatment means that the agent may be administered prior to, together with, or after the additional treatment, or a combination thereof.

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, "relative abundance" refers to amount determined from electrospray ionization mass spectrometry. Mass spectrometry is an analytical technique that can provide both qualitative (structure) and quantitative (molecular mass or concentration) information on analyte molecules after their conversion to ions. The molecules of interest are first introduced into the ionization source of the mass spectrometer, where they are first ionized to acquire positive or negative charges. The ions then travel through the mass analyzer and arrive at different parts of the detector according to their mass to charge (m/z) ratio. After the ions make contact with the detector, useable signals are generated and recorded by a computer system. The computer displays the signals graphically as a mass spectrum showing the relative abundance of the signals according to their m/z ratio.

Extracts Exhibit Quorum Quenching Activity

To test the anti-infective properties of *Schinus terebinthifolia*, a suite of bioactive compounds was identified in *S. terebinthifolia* fruits that are able to inhibit the agr system in *Staphylococcus aureus* without killing or inhibiting growth. As the global regulator of virulence in *S. aureus*, the agr system is responsible for initial infection of host cells, evasion of the host immune system, quorum sensing, and the destruction of tissues with toxins and other enzymes. Through inhibition of the agr system with the use of small molecule inhibitors isolated from *S. aureus* virulence could be decreased, thus limiting the severity of disease and increasing efficacy of existing antibiotics.

Figure 6:
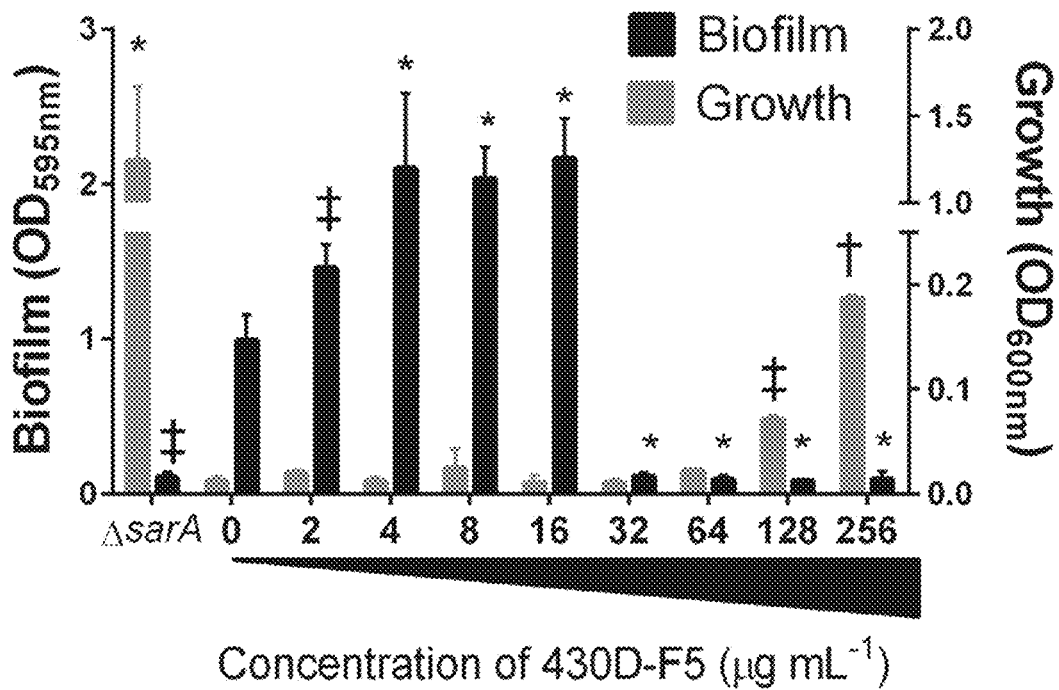
FIG. 6 shows data on the impact of 430D-F5 on *S. aureus* biofilm formation and planktonic growth in a biofilm model with crystal violet stained biofilm in 96-well plates. The optical density (OD595 nm) of the crystal violet eluent is plotted against the OD600 nm for planktonic cells, measured by transfer of the well supernatants to a new 96-well plate.

One main concern and point of debate in the literature concerning the utility and limitations of anti-virulence drugs to treat *S. aureus* infection is the potential for activation of other virulence pathways, such as biofilm formation. Here, studies indicate while at lower concentrations (2-16 μg mL$^{-1}$) there was an increase in biofilm formation, there was also an abrupt drop in attached biofilm observed at 32 μg mL$^{-1}$, exhibiting a phenotype similar to that of the ΔsarA control (FIG. 6). This suggests that at doses required for quorum quenching activity, biofilm formation will also be inhibited.

In vivo assessment of the most active fraction (430D-F5) demonstrated inhibition of the severity of necrosis at an infection site. Furthermore, a model of real time in vivo tracking of agr activity was applied to monitor drug activity. It is contemplates that 430D-F5 and isolated small molecules are useful in preventing or treating established infections both alone and in combination with another antibiotic or combination antibiotic therapy.

Fluorescent reporter strains were used to identify fractions of 430D (the butanol partition of *S. terebinthifolia* fruits) that exhibit quorum quenching activity. The *S. terebinthifolia* fruit extracts (430, 430D, 430D-F5) inhibit the hemolytic capacity of *S. aureus* isolates. Fraction (430D-F5) was the most potent. To confirm that the agr-quenching activity observed with reporters also leads to quenching of exotoxin production, levels of δ-toxin were quantified in the bacterial supernatant. One major benefit of using virulence inhibitors with current extracts or one or more compounds therein with a classical antibiotic is the potential for increased antibiotic efficacy. By blocking the toxins responsible for immune response damage, the antibiotics and immune system can work more in concert to eliminate the bacteria.

In certain embodiments, the extract comprises a mixture of compounds having at least one component from each of the following groups a) to d): a) a compound having a molecular formula of $C_{30}H_{17}O_{10}$; b) a compound having a molecular formula of $C_{30}H_{21}O_{10}$; c) a compound having a molecular formula of $C_{30}H_{45}O_4$; and d) a compound having a molecular formula of $C_{30}H_{45}O_4$.

In certain embodiments, the extract comprises a mixture of compounds having at least one component from each of the following groups a) to d): a) a compound selected from amentoflavone, agathisflavone, and robustaflavone; b) a compound selected from chamaejasmin, tetrahydroamentoflavone, and tetrahydrorobustaflavone: c) a compound selected from albsapogenin, (13α, 14β, 17α,20R,24Z)-3α-hydroxy-21-oxolanosta-8,24-dien-26-oic acid, (13α,14β, 17α,20S,24Z)-3α-hydroxy-21-oxolanosta-8,24-dien-26-oic acid, (3α,13α,14β,17α,24Z)-3-hydroxy-7-oxo-lanosta-8,24-dien-26-oic acid, and mollinoic acid; and d) isomasticadienonalic acid.

Contemplated topical formulations for skin flares (i.e. for atopic dermatitis or other infections related to a disrupted skin barrier) may be combined with the anti-virulence drug including: topical steroids, anti-inflammatory agents, and promoters of skin barrier function or skin moisturizers such as ceramide, glycerin, colloidal oatmeal.

In certain embodiments the disclosure contemplates that an extract or one or more compounds in an extract disclosed herein may be used as a virulence inhibitor applications optionally in combination with other antibacterial agents for prevention of disease onset and treatment such as in medical device coatings (medical implants and tools, IV catheters), wound dressings (embedded in gauze bandages), wound rinses (i.e. surgical rinses), wound-vacuum systems, whole body baths (e.g., in combo with bleach baths for treatment of skin flares for atopic dermatitis/eczema), soaps, personal care products (body washes, lotions, soaps) for high risk patients or for populations with high risk of exposure (e.g. athletes using common sports equipment in gym) human and veterinary applications (e.g. anti-infectives for companion animals, race horses, etc.)

Methods of Use

In certain embodiments, this disclosure relates to methods of treating or preventing bacterial infections comprising administering or contacting a formula comprising an extract or one or more compounds in an extract as disclosed herein to a subject in need thereof. In certain embodiments, the formula is administered in combination with another antibiotic agent.

In further embodiments, the subject is co-administered with an antibiotic selected from the group comprising of sulfonamides, diaminopyrimidines, quinolones, beta-lactam antibiotics, cephalosporins, tetracyclines, notribenzene derivatives, aminoglycosides, macrolide antibiotics, polypeptide antibiotics, nitrofuran derivatives, nitroimidazoles, nicotinic acid derivatives, polyene antibiotics, imidazole derivatives or glycopeptide, cyclic lipopeptides, glycylcyclines and oxazolidinones. In further embodiments, these antibiotics include but are not limited to sulphadiazine, sulfones—[dapsone (DDS) and para-aminosalicylic (PAS)], sulfanilamide, sulfamethizole, sulfamethoxazole, sulfapyridine, trimethoprim, pyrimethamine, nalidixic acids, norfloxacin, ciproflaxin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cephaloglycin, cefalonium, cefaloridine, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefotetan, cefoxitin, cefcapene, cefdaloxime, cefdinir, cefditoren, cefetamet, cefixime, cefinenoxime, cefodizime, cefoperazone, cefotaxime, cefotiam, cefpimizole, cefpiramide, cefpodoxime, cefteram, ceftibuten, ceftiofur, ceftizoxime, ceftriaxone, cefoperazone, ceftazidime, cefepime), moxalactam, carbapenems (imipenem, ertapenem, meropenem) monobactams (aztreonam)oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomycin, netilmicin, streptomycin, tobramycin, azithromycin, clarithromycin, dirithromycin, erythromycin, roxithromycin, telithromycin, colistin, bacitracin, tyrothricin, nitrofurantoin, furazolidone, metronidazole, tinidazole, isoniazid, pyrazinamide, ethionamide, nystatin, amphotericin-B, hamycin, miconazole, clotrimazole, ketoconazole, fluconazole, rifampicin, lincomycin, clindamycin, spectinomycin, fosfomycin, loracarbef, polymyxin B, polymyxin B Sulfate, procaine, ramoplanin, teicoplanin, vancomycin, and/or nitrofurantoin.

In certain embodiments, this disclosure relates to methods of treating or preventing a toxin-mediated bacterial infection comprising administering an effective amount of an *Schinus* extract or compounds contained therein to a subject in need thereof, including a subject at risk of, exhibiting symptoms of, or diagnosed with a staphylococcal scalded skin syndrome (esp. in neonates), abscesses, necrotizing fasciitis, sepsis, atopic dermatitis (eczema) and more.

In certain embodiments, the subject is at risk of, exhibiting symptoms of, or diagnosed with toxic shock syndrome, scalded skin syndrome, abscesses, furuncles, cellulitis, folliculitis, bloodstream infections, medical device infections, pneumonia, osteomyelitis, staphylococcal food poisoning, skin and soft tissue infections, endocarditis, eczema, atopic dermatitis, psoriasis, impetigo, septic arthritis, brain abscess, burn wounds, venous ulcers, diabetic foot ulcers, surgical wounds, post-operation infections, carbuncles, meningitis, bacteremia, necrotizing pneumonia, or necrotizing fasciitis.

In certain embodiments, the disclosure contemplates methods of preventing bacterial infections by applying extracts or one or more compounds in extracts disclosed herein in a tampon for prevention against adverse effects associated with vaginal area infections and possibly bladder infections, e.g., toxic shock syndrome. As used herein a "tampon" refers to device containing an absorbent material, configured to be inserted into a vagina to absorb menstrual flow and typically expand during use, typically in the shape of a cylinder. Tampons may expand axially (increase in length), while digital tampons will expand radially (increase in diameter). Most tampons have a cord or string for removal. Typical tampon materials include cloth, fibers, cotton, or rayon, or a blend of rayon and cotton.

Bacterial toxins may cause toxic shock syndrome (TSS). Enterotoxin type B or TSST-1 of *Staphylococcus aureus* are believed to cause TSS. Streptococcal TSS is sometimes referred to as toxic shock-like syndrome (TSLS) or streptococcal toxic shock syndrome (STSS). CDC criteria for diagnosing staphylococcal toxic shock syndrome is based on 1) a body temperature of greater than 38.9° C. (102° F.) 2) a Systolic blood pressure of greater than 90 mmHg 3) diffuse macular erythroderma 4) desquamation (especially of the palms and soles) 1-2 weeks after onset 5) involvement of three or more organ systems: gastrointestinal (vomiting, diarrhea), muscular: severe myalgia or creatine phosphokinase level at least twice the upper limit of normal for laboratory, mucous membrane hyperemia (vaginal, oral, conjunctival), kidney failure (serum creatinine >2 times normal), liver inflammation (bilirubin, AST, or ALT >2 times normal), low platelet count (platelet count <100,000/mm$^3$), Central nervous system involvement (confusion without any focal neurological findings) and 6) Negative results of: blood, throat, and CSF cultures for other bacteria (besides *S. aureus*) negative serology for *Rickettsia* infection, leptospirosis, and measles. Cases are classified as probable if five of the six criteria above are met.

In certain embodiments, the disclosure contemplates methods of preventing general transmission of bacterial through use of extracts and one or more compounds in an extract disclosed herein as a general agent formulated into a spray or wipe product, paper or fiber based cloth. For example, one can use such a product to treat athletic equipment (football pads, bench presses, gym surfaces), where invasive toxin mediated *staphylococcus* often lurks and causes infections in healthy people through toxin production.

In certain embodiments, the disclosure relates to methods of treating acne comprising administering an effective amount of a composition comprising an extract or one or more compounds in an extract as disclosed herein to a subject at risk of, exhibiting symptoms of, or diagnosed with acne, blackheads, papules, pustules or nodules. In certain embodiments, the subject is undergoing puberty, between 10 and 20 years of age. In certain embodiments, the subject is a female, and the composition is administered within seven days of the beginning of a menstrual cycle. Administration may be by topical application through hand or by spray of a liquid or lotion containing an extract or one or more compounds in an extract disclosed herein.

Extracts and Compounds

In certain embodiments, an extract is made by the process of extracting a mixture of compounds from the leaves, roots, bark, stem, fruit, or branches of a *Schinus* plant such as *Schinus terebinthifolia*. Other contemplated plants include: *Schinus andina* and varieties (*andina* and *subtridentata*), *Schinus angustifolia, Schinus antiarthritica, Schinus areira, Schinus bituminosa, Schinus bonplandiana, Schinus brasiliensis, Schinus bumelioides, Schinus canrerae, Schinus chebataroffi, Schinus chichita, Schinus crenata, Schinus dentata, Schinus dependens* and varieties (*alfa, arenicola, brevifolia, crenata, grandifolia, longifolia, obovata, ovata, paraguarensis, parvifolia, patagonica, subintegra, tomentosa*), *Schinus discolor, Schinus diversifolia, Schinus engleri* and varieties (*engleri, uruguayensis*), *Schinus fagara, Schinus fasciculate* and varieties (*arenaria, arenicola, boliviensis, fasciculata*), *Schinus ferox, Schinus* gracilipes and varieties (*gracilipies, pilosus*), *Schinus huigan, Schinus huyngan* and varieties (*heterophyllus, longifolius, obovatus, subtridentata, undulate*), *Schinus indicus, Schinus johnstonii, Schinus latifolius* and varieties (*tomentosus*), *Schinus lentiscifolius* and varieties (*angustifolia, flexuosa, subobtusa*), *Schinus* leucocarpus, *Schinus limonia, Schinus longifolia* and varieties (*longifolia, paraguarensis*), *Schinus marchandii, Schinus maurioides, Schinus mellisii, Schinus meyeri, Schinus microphylla. Schinus microphyllus, Schinus molle* and varieties (*areira, argentifolius, hassleri, huigan, huyngan, molle, rusbyi*), *Schinus molleoides, Schinus montanus* and varieties (*crenuloides, patagonicus*), *Schinus mucronulatus, Schinus myricoides, Schinus myrtifolia, Schinus occidentalis, Schinus odonellii, Schinus paraguarensis, Schimis patagonicus* and varieties (*crenuloides, patagonicus*), *Schinus pearcei. Schinus pilifera* and varieties (*boliviensis, cabrerae, pilifer*), *Schinus polygama* and varieties (*australis, chubutensis, crenata, fasciculata, heterophylla, ovata, parviflora, patagonica*), *Schinus polygamus, Schinus praecox, Schinus pubescens, Schinus ramboi, Schinus resinosus, Schinus rhoifolia, Schinus roigii, Schinus sinuatus, Schinus spinosus, Schinus tenuifolius, Schinus terebinthifolius* and varieties (*acutifolia, damaziana, glaziovana, pohlianus, raddiana, rhoifolia, selloana, terebinthifolia, ternifolia*), *Schinus terebinthifolius, Schinus ternifolia, Schinus tomentosa,*

*Schinus tragodes, Schinus veltinus, Schinus venturii, Schinus weinmannifolius* and varieties (*angustifolius, dubius, glabrescens, hassleri, intermedius, pauciflorus, paucijuga, pubescens, riedelianus, ridelianus, weinmannifolius*) and hybrids thereof.

In certain embodiments, the extracting process comprises the step of mixing the fruit from the plant with a polar solvent, such as a liquid comprising methanol, ethanol, ethyl acetate, n-butanol, acetonitrile, acetone, methylene chloride or chloroform, under conditions such that a mixture of compounds in the fruit dissolves in the solvent. In certain embodiments, the process further comprises the step of removing the solvent by evaporation from the mixture of compounds. In certain embodiments, the process further comprises the step of purifying the mixture of compounds by liquid chromatography through a solid absorbent, e.g., wherein the solid absorbent comprises silica gel or alumina.

In certain embodiments, the disclosure relates to extracts comprising a fruit derived mixture of compounds from a *Schinus* plant wherein the extracting process comprises the steps of: mixing a fruit with methanol under conditions such that fruit compounds dissolves in the methanol and removing the methanol providing a methanol derived mixture of compounds; partitioning the methanol derived mixture of compounds with hexane and water providing a water derived mixture of compounds; partitioning the water derived mixture of compounds with ethyl acetate and water providing a second water derived mixture of compounds; partitioning the second water derived mixture of compounds by mixing the water with n-butanol under conditions such that fruit compounds dissolve in the butanol and removing the n-butanol providing an n-butanol derived mixture of compounds; and purifying the n-butanol derived mixture of compounds by liquid chromatography.

Chromatography refers to the separation of a mixture of compounds dissolved in a fluid called the mobile phase, which carries the compounds through a structure holding another material called the stationary phase. The various compounds or components of the mixture travel at different speeds, causing them to separate. The separation is based on differential partitioning between the mobile and stationary phases. Subtle differences in a partition coefficient of each compound result in differential retention on the stationary phase and thus changing the separation.

In normal-phase chromatography, the stationary phase is polar. In reversed phase, the stationary phase is nonpolar. Typical stationary phases for normal-phase chromatography are silica or organic moieties with cyano and amino functional groups. For reversed phase, alkyl hydrocarbons are the preferred stationary phase. Examples are solid supports containing a surface conjugated with a hydrocarbon chain, e.g., octadecyl (C18), octyl (C8), and butyl (C4).

In normal-phase chromatography, the least polar compounds elute first and the most polar compounds elute last. The mobile phase typically consists of a nonpolar solvent such as hexane or heptane mixed with a slightly more polar solvent such as isopropanol, ethyl acetate, n-butanol, or chloroform. Retention to the stationary phase decreases as the amount of polar solvent in the mobile phase increases. In reversed phase chromatography, the most polar compounds elute first with the most nonpolar compounds eluting last. The mobile phase is generally a binary mixture of water and a miscible polar organic solvent like methanol, acetonitrile or THF.

In certain embodiments, methods of extraction comprise mixing the fruit of a *Schinus* plant with an water miscible carbon containing solvent, e.g., such as a protic solvent, an alcohol, methanol, ethanol, 1-propanol, 2-propanol, tetrahydrofuran, acetone, acetic acid, 1,4-dioxane or mixture providing a concentrate with a mixture of compounds and substantially removing the solvent from the concentrate, purifying the solvent derived concentrate to less than 5%, 1%, or 0.5% by weight of the solvent used in the extraction, e.g., evaporating the protic solvent and/or optionally in combination with mixing the concentrate with water, sonicating the water, freezing the water to provide ice, and removing the ice by sublimation (e.g. in a vacuum of low pressure) wherein said purification methods may be repeated in combination. In certain embodiments, the method further comprises suspending the solvent derived concentrate in water and optionally extract impurities in a hydrocarbon solvent such as cyclohexane, heptane, hexane, pentane, 2,2,4-trimethylpentane, separating the hydrocarbon from the water providing a water layer. In certain embodiments, the method further comprises mixing the water layer with a solvent that is immiscible in water (polar and/or aprotic), e.g., such as ethyl acetate, diethyl ether, methyl tertbutyl ether, n-butanol, toluene, methylene chloride, carbon tetrachloride, 1,2-dichloroethant, and/or chloroform, and purifying the solvent to provide a second solvent derived concentrate. In further embodiments, the second derived concentrate is purified one or more times by liquid chromatography, e.g., normal phase chromatography.

In certain embodiments, the disclosure contemplates that liquid chromatography includes using a mobile phase utilizing with a solvent that is immiscible in water (polar and/or aprotic) and increasing amounts of an alcohol. In certain embodiments, the disclosure contemplates that liquid chromatography includes using a mobile phase utilizing dichloromethane and increasing amounts of methanol. In certain embodiments, the disclosure contemplates that liquid chromatography includes using a mobile phase utilizing ethyl acetate and increasing amounts of methanol. In certain embodiments, the disclosure contemplates that liquid chromatography includes using a mobile phase utilizing dichloromethane and increasing amounts of n-butanol. In certain embodiments, the disclosure contemplates that liquid chromatography includes using a mobile phase utilizing ethyl acetate and increasing amounts of n-butanol. In certain embodiments, the disclosure contemplates that liquid chromatography includes using a mobile phase utilizing dichloromethane and increasing amounts of ethanol. In certain embodiments, the disclosure contemplates that liquid chromatography includes using a mobile phase utilizing ethyl acetate and increasing amounts of ethanol. In certain embodiments, the disclosure contemplates that liquid chromatography includes using a mobile phase utilizing dichloromethane and increasing amounts of n-propanol. In certain embodiments, the disclosure contemplates that liquid chromatography includes using a mobile phase utilizing ethyl acetate and increasing amounts of n-propanol.

Pharmaceutical Formulation

In certain embodiments, the disclosure relates to a pharmaceutical formulation comprising an extract or one or more compounds in an extract disclosed herein and a pharmaceutically acceptable excipient or additive. In certain embodiments, the disclosure relates to a lotion, liquid, or gel formulation optionally further comprising an antibiotic agent, a topical steroid, an anti-inflammatory agent, a promoter of skin barrier function, a skin moisturizer or combinations thereof.

Examples of antibiotics include but are not limited to sulphadiazine, sulfones—[dapsone (DDS) and para-aminosalicylic (PAS)], sulfanilamide, sulfamethizole, sulfamethoxazole, sulfapyridine, trimethoprim, pyrimethamine, nalidixic acids, norfloxacin, ciprofloxacin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cephaloglycin, cefalonium, cefaloridine, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefotetan, cefoxitin, cefcapene, cefdaloxime, cefdinir, cefditoren, cefetamet, cefixime, cefmenoxime, cefodizime, cefoperazone, cefotaxime, cefotiam, cefpimizole, cefpiramide, cefpodoxime, cefteram, ceftibuten, ceftiofur, ceftizoxime, ceftriaxone, cefoperazone, ceftazidime, cefepime), moxalactam, carbapenems (imipenem, ertapenem, meropenem) monobactams (aztreonam)oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomycin, netilmicin, streptomycin, tobramycin, azithromycin, clarithromycin, dirithromycin, erythromycin, roxithromycin, telithromycin, colistin, bacitracin, tyrothricin, nitrofurantoin, furazolidone, metronidazole, tinidazole, isoniazid, pyrazinamide, ethionamide, nystatin, amphotericin-B, hamycin, miconazole, clotrimazole, ketoconazole, fluconazole, rifampicin, lincomycin, clindamycin, spectinomycin, fosfomycin, loracarbef, polymyxin B, polymyxin B Sulfate, procaine, ramoplanin, teicoplanin, vancomycin, and/or nitrofurantoin.

Examples of steroids include hydrocortisone, hydrocortisone valerate, hydrocortisone 17-butyrate, mometasone, mometasone furoate, halobetasol propionate, desonide, desoximetasone, fluocinolone acetonide, alclometasone dipropionate, flurandrenolide, fluticasone propionate, diflucortolone, diflucortolone valerate, diflorasone diacetate, clobetasol, clobetasone butyrate, clobetasol propionate, betamethasone dipropionate, betamethasone valerate, beclomethasone, budesonide, flunisolide, fluocinonide, triamcinolone, triamcinolone acetonide, methylprednisolone, methylprednisolone aceponate, prednicarbate, prednisolone, and prednisone and alternate salts thereof. Examples of contemplated anti-inflammatory agents are aspirin, celecoxib, diclofenac, diflunisal, etodolac, ibuprofen, indomethacin, ketoprofen, naproxen, oxaprozin, and piroxicam.

In certain embodiments, the disclosure relates to a pharmaceutical composition comprising an extract or one or more compounds in an extract disclosed herein formulated with an enteric coating. In certain embodiments, the disclosure relates to a pharmaceutical formulation of an extract or one or more compounds in an extract disclosed herein which protect the compositions from the acidity and enzymatic action of gastric secretions. In certain embodiments, the pharmaceutical formulations contain an extract or one or more compounds in an extract disclosed herein in a composition with an enteric coating along with another pharmaceutically acceptable vehicle. In certain embodiments, compositions comprising an extract or one or more compounds in an extract disclosed herein may be directly-compressible without excipients, into a tablet of pharmaceutically acceptable hardness, e.g., compressed into a tablet, optionally with a lubricant, such as but not limited to magnesium stearate, and enteric coated. In another embodiment, the pharmaceutical compositions containing an extract or one or more compounds in an extract disclosed herein alternatively include one or more substances that either neutralize stomach acid and/or enzymes or are active to prevent secretion of stomach acid.

The pharmaceutical composition can be formulated for oral administration as, for example but not limited to, drug powders, crystals, granules, small particles (which include particles sized on the order of micrometers, such as microspheres and microcapsules), particles (which include particles sized on the order of millimeters), beads, microbeads, pellets, pills, microtablets, compressed tablets or tablet triturates, molded tablets or tablet triturates, and in capsules, which are either hard or soft and contain the composition as a powder, particle, bead, solution or suspension. The pharmaceutical composition can also be formulated for oral administration as a solution or suspension in an aqueous liquid, as a liquid incorporated into a gel capsule or as any other convenient formulation for administration, or for rectal administration, as a suppository, enema or other convenient form.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

Suitably, the pharmaceutical composition of the disclosure comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic infusion. It is typically isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solutions, Hank's solution, and other aqueous physiologically balanced salt solutions. The pH of the composition of the disclosure is suitably adjusted and buffered in order to be appropriate for use in humans or animals, typically at a physiological or slightly basic pH (between about pH 8 to about pH 9, with a special preference for pH 8.5). Suitable buffers include phosphate buffer (e.g. PBS), bicarbonate buffer and/or Tris buffer. A typical composition is formulated in IM saccharose, 150 mM NaCl, 1 mM MgCl2, 54 mg/l Tween 80, 10 mM Tris pH 8.5. Another typical composition is formulated in 10 mg/ml mannitol, 1 mg/ml HSA, 20 mM Tris, pH 7.2, and 150 mM NaCl.

The pharmaceutical formulation can also include any type of pharmaceutically acceptable excipients, additives or vehicles. For example, but not by way of limitation, diluents or fillers, such as dextrates, dicalcium phosphate, calcium sulfate, lactose, cellulose, kaolin, mannitol, sodium chloride, dry starch, sorbitol, sucrose, inositol, powdered sugar, bentonite, microcrystalline cellulose, or hydroxypropylmethylcellulose may be added to the composition comprising an extract or one or more compounds in an extract disclosed herein to increase the bulk of the composition. Also, binders, such as but not limited to, starch, gelatin, sucrose, glucose, dextrose, molasses, lactose, acacia gum, sodium alginate, extract of Irish moss, ganwar gum, ghatti gum, mucilage of isabgol husks, carboxymethylcellulose, methylcellulose, polyvinylpyrrolidone, Veegum and starch arabogalactan, polyethylene glycol, ethylcellulose, and waxes, may be added to the formulation to increase its cohesive qualities. Additionally, lubricants, such as but not limited to, talc, magnesium stearate, calcium stearate, stearic acid, hydrogenated vegetable oils, polyethylene glycol, sodium benzoate, sodium acetate, sodium chloride, leucine, carbowax, sodium lauryl sulfate, and magnesium lauryl sulfate may be added to the formulation. Also, glidants, such as but not limited to, colloidal silicon dioxide or talc may be added to improve the flow characteristics of a powdered formulation. Finally, disintegrants, such as but not limited to, starches, clays, celluloses, algins, gums, crosslinked polymers (e.g., croscarmellose, crospovidone, and sodium starch glycolate), Veegum, methylcellulose, agar, bentonite, cellulose and wood products, natural sponge, cation-exchange resins, alginic acid, guar gum, citrus pulp, carboxymethylcellulose, or sodium lauryl sulfate with starch may also be added to facilitate disintegration of the formulation in the intestine.

In certain embodiments, the formulation contains a directly compressible composition comprising an extract or one or more compounds in an extract disclosed herein but no excipients, additives or vehicles other than an enteric coating; however, the formulation may contain a lubricant, such as but not limited to, magnesium stearate. Preferably, the directly compressed formulation is formulated as a tablet of pharmaceutically acceptable hardness (greater than 6 kp, preferably 8-14 kp, and more preferably 10-13 kp).

Polymers which are useful for the preparation of enteric coatings include, but are not limited to, shellac, starch and amylose acetate phthalates, styrene-maleic acid copolymers, cellulose acetate succinate, cellulose acetate phthalate (CAP), polyvinylacetate phthalate (PVAP), hydroxypropylmethylcellulose phthalate (grades HP-50 and HP-55), ethylcellulose, fats, butyl stearate, and methacrylic acid-methacrylic acid ester copolymers with acid ionizable groups ("EUDRAGIT™"), such as "EUDRAGIT™ L 30D", "EUDRAGIT™ RL 30D", "EUDRAGIT™ RS 30D", "EUDRAGIT™ L 100-55", and "EUDRAGIT™ L 30D-55".

Application of the enteric coating to composition can be accomplished by any method known in the art for applying enteric coatings. For example, but not by way of limitation, the enteric polymers can be applied using organic solvent based solutions containing from 5 to 10% w/w polymer for spray applications and up to 30% w/w polymer for pan coatings. Solvents that are commonly in use include, but are not limited to, acetone, acetone/ethyl acetate mixtures, methylene chloride/methanol mixtures, and tertiary mixtures containing these solvents. Some enteric polymers, such as methacrylic acid-methacrylic acid ester copolymers can be applied using water as a dispersant.

Furthermore, plasticizers can be added to the enteric coating to prevent cracking of the coating film. Suitable plasticizers include the low molecular weight phthalate esters, such as diethyl phthalate, acetylated monoglycerides, triethyl citrate, polyethyl glycoltributyl citrate and triacetin. Generally, plasticizers are added at a concentration of 10% by weight of enteric coating polymer weight. Other additives such as emulsifiers, for example detergents and simethicone, and powders, for example talc, may be added to the coating to improve the strength and smoothness of the coating. Additionally, pigments may be added to the coating to add color to the pharmaceutical formulation.

In certain embodiments, the composition comprising an extract or one or more compounds in an extract disclosed herein is formulated with a compound or compounds which neutralize stomach acid. Alternatively, the pharmaceutical composition containing an extract or one or more compounds in an extract disclosed herein is administered either concurrent with or subsequent to administration of a pharmaceutical composition which neutralize stomach acid. Compounds, such as antacids, which are useful for neutralizing stomach acid include, but are not limited to, aluminum carbonate, aluminum hydroxide, bismuth subnitrate, bismuth subsalicylate, calcium carbonate, dihydroxyaluminum sodium carbonate, magaldrate, magnesium carbonate, magnesium hydroxide, magnesium oxide, and mixtures thereof.

In certain embodiments, composition comprising an extract or one or more compounds in an extract disclosed herein is administered with a substance that inactivates or inhibits the action of stomach enzymes, such as pepsin. Alternatively, the pharmaceutical composition containing the proanthocyanidin polymer composition is administered either concurrent with or subsequent to administration of a pharmaceutical composition active to inactivate or inhibit the action of stomach enzymes. For example, but not by way of limitation, protease inhibitors, such as aprotin, can be used to inactivate stomach enzymes.

In certain embodiments, the composition comprising an extract or one or more compounds in an extract disclosed herein is formulated with a compound or compounds which inhibit the secretion of stomach acid. Alternatively, the pharmaceutical composition is administered either concurrent with or subsequent to administration of a pharmaceutical composition active to inhibit the secretion of stomach acid. Compounds which are useful for inhibiting the secretion of stomach acid include, but are not limited to, ranitidine, nizatidine, famotidine, cimetidine, and misoprostol.

Cosmetic Formulations and Personal Care Products

In certain embodiments, the disclosure relates to a cosmetic formulation comprising an extract or one or more compounds in an extract disclosed herein and cosmetically acceptable excipient or additive. In certain embodiments, the disclosure relates to a solid or liquid soap or lotion comprising an extract or one or more compounds in an extract disclosed herein and a fatty acid.

In certain embodiments, additives can be selected from the group consisting of oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils and dyes.

In certain embodiments, additives are selected from the group consisting of surfactants, emulsifiers, fats, waxes, stabilizers, deodorants, antiperspirants, antidandruff agents and perfume oils.

As used herein, cosmetic preparations can mean care agents. Care agents are understood as meaning care agents for skin and hair. These care agents include, inter alia, cleansing and restorative action for skin and hair.

In certain embodiments, preparations may be cosmetic and/or dermopharmaceutical preparations, e.g. hair shampoos, hair lotions, foam baths, shower baths, creams, gels, lotions, alcoholic and aqueous/alcoholic solutions, emulsions, wax/fat compositions, stick preparations, powders or ointments.

Surfactants (or Surface-active substances) that may be present are anionic, non-ionic, cationic and/or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefin sulfonates, alkyl ether sulfonates, glycerol ether sulfonates, α-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants contain polyglycol ether chains, these may have a conventional homologous distribution, but preferably have a narrowed homologous distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucuronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these may have a conventional homologous distribution, but preferably have a narrowed homologous distribution. Typical examples of cationic surfactants are quaternary ammonium compounds, e.g. dimethyldistearyl-ammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazolinium-betaines and sulfobetaines. Said surfactants are known compounds. With regard to structure and preparation of these substances, reference may be made to relevant review works.

Typical examples of particularly suitable mild, i.e. particularly skin-compatible surfactants are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, the latter preferably based on wheat proteins.

Suitable oily bodies are, for example, alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols, in particular dioctyl malates, esters of linear and/or branched fatty acids with polyhydric alcohols (for example propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, for example dicaprylyl carbonates (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, for example dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, for example squalane, squalene or dialkylcyclohexanes.

Suitable emulsifiers are, for example, nonionogenic surfactants from at least one of the following groups:
  addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical;
  alkyl and/or alkenyl oligoglycosides having 8 to 22 carbon atoms in the alk(en)yl radical and the ethoxylated analogs thereof;
  addition products of from 1 to 15 mol of ethylene oxide onto castor oil and/or hydrogenated castor oil;
  addition products of from 15 to 60 mol of ethylene oxide onto castor oil and/or hydrogenated castor oil;
  partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;
  partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;
  mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof, wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen® grades (TR-1, TR-2) from Goodrich;

polyalkylene glycols and glycerol carbonate.

The addition products of ethylene oxide and/or propylene oxide onto fatty alcohols, fatty acids, alkylphenols or onto castor oil are known, commercially available products. These are homologous mixtures whose average degree of alkoxylation corresponds to the ratio of the amounts of ethylene oxide and/or propylene oxide and substrate with which the addition reaction is carried out. C12/18-fatty acid mono- and diesters of addition products of ethylene oxide onto glycerol are known as refatting agents for cosmetic preparations.

Alkyl and/or alkenyl oligoglycosides can be prepared by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value that is based on a homologous distribution customary for such technical-grade products.

Typical examples of suitable partial glycerides are hydroxy stearic acid monoglyceride, hydroxy stearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linoleic acid monoglyceride, linoleic acid diglyceride, erucic acid monoglyceride, erucic acid diglyceride, tartaric acid monoglyceride, tartaric acid diglyceride, citric acid monoglyceride, citric acid diglyceride, malic acid mono-glyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide onto said partial glycerides.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of 1 to 30 mol, preferably 5 to 10 mol, of ethylene oxide onto said sorbitan esters.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifiers. The term "zwitterionic surfactants" refers to those surface-active compounds that carry at least one quaternary ammonium group and at least one carboxylate and one sulfonate group in the molecule. Particularly suitable zwitterionic surfactants are the betaines, such as N-alkyl-N,N-dimethylammonium glycinates, for example cocoalkyldimethylammonium glycinate, N-acylaminopropyl-N,N-dimethylammonium glycinates, for example cocoacyl-amino-propyldimethylammonium glycinate, and 2-alkyl-3-carboxymethyl-3-hydroxyethylimidazolines having in each case 8 to 18 carbon atoms in the alkyl or acyl group, and cocoacylamino-ethylhydroxyethyl-carboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds that, apart from a $C_{8/18}$-alkyl or -acyl group in the molecule, contain at least one free amino group and at least one —$CO_2H$ or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyl-taurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkyl aminopropionate, cocoacyl-aminoetbyl aminopropionate and $C_{12/18}$-acylsarcosine. Finally, cationic surfactants are also suitable emulsifiers, those of the ester quat type, preferably methylquaternized difatty acid triethanolamine ester salts, being particularly preferred.

Fats and waxes that can be used are described in the following text. Typical examples of fats are glycerides, i.e. solid or liquid vegetable or animal products which consist essentially of mixed glycerol esters of higher fatty acids, suitable waxes are inter alia natural waxes, for example candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), for example montan ester waxes, sasol waxes, hydrogenated jojoba waxes, and synthetic waxes, for example polyalkylene waxes and polyethylene glycol waxes. In addition to the fats, suitable additives are also fat-like substances, such as lecithins and phospholipids.

The term "lecithins" is understood by the person skilled in the art as meaning those glycerophospholipids which form from fatty acids, glycerol, phosphoric acid and choline by esterification. Lecithins are thus frequently also known as phosphatidylcholines (PC). Examples of natural lecithins which may be mentioned are the cephalins, which are also referred to as phosphatidic acids and represent derivatives of 1,2-diacyl-sn-glycerol-3-phosphoric acids. By contrast, phospholipids are usually understood as meaning monoand, preferably, diesters of phosphoric acid with glycerol (glycerophosphates), which are generally considered to be fats. In addition, sphingosines and sphingolipids are also suitable.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, for example fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Bodying agents and thickeners that can be used are described in the following text. Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, aerosol grades (hydrophilic silicas), polysaccharides, in particular xanthan gum, guar, agar, alginates and Tyloses, carboxymethylcellulose and hydroxyethylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone, surfactants, for example ethoxylated fatty acid glycerides, esters of fatty acids with polyols for example pentaerythritol or trimethylolpropane, fatty alcohol ethoxylates having a narrowed homolog distribution or alkyl oligoglucosides, and electrolytes such as sodium chloride and ammonium chloride.

Superfatting agents which can be used are for example lanolin and lecithin, and polyethoxylated or acylated lanolin and lecithin derivatives, polyol fatty acid esters, monoglycerides and fatty acid alkanolamides, the latter also serving as foam stabilizers.

Stabilizers which can be used are metal salts of fatty acids, for example magnesium, aluminium and/or zinc stearate or ricinoleate.

Polymers that can be used are described in the following text. Suitable cationic polymers are, for example, cationic cellulose derivatives, for example a quaternized hydroxyethylcellulose obtainable under the name Polymer JR 400® from Amerchol, cationic starch, copolymers of diallylammonium salts and acryl amides, quaternized vinylpyrrolidone-vinylimidazole polymers, for example Luviquat® (BASF), condensation products of polyglycols and amines, quaternized collagen polypeptides, for example lauryldimonium hydroxypropyl hydrolysed collagen (Lamequat® L/Grünau), quaternized wheat polypeptides, polyethyleneimine, cationic silicone polymers, for example amodimethicones, copolymers of adipic acid and dimethylaminohydroxypropyldiethylenetriamine (Cartaretins®/Sandoz), copolymers of acrylic acid with dimethyl diallylammonium chloride (Merquat® 550/Chemviron), polyaminopolyamides and cross linked water-soluble polymers thereof, cationic chitin derivatives, for example quaternized chitosan, optionally in microcrystalline dispersion, condensation products from dihaloalkyls, for example dibromobutane with bisdialkylamines, for example bis-dimethylamino-1,3-propane, cationic guar gum, for example Jaguar® CBS, Jaguar® C-17, Jaguar® C-16 from Celanese, quaternized ammonium salt polymers, for example Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamidemethyl methacrylate-tert-butylamino-ethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates.

Deodorants and antimicrobial agents that can be used are described in the following text. Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents. Suitable antimicrobial agents are, in principle, all substances effective against gram-positive bacteria, for example 4-hydroxybenzoic acid and its salts and esters, N-(4-chlorophenyl)-N'-(3,4-dichloro-phenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methyl-ethyl)phenol, 2-benzyl-4-chlorophenol, 3-(4-chlorophenoxy)-1,2-propanediol, 3-iodo-2-propynyl butylcarbamate, chlorohexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, for example n-octylsalicylamide or n-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxy-carboxylic acids and esters thereof, for example citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", for example extracts of labdanum or *styrax* or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, for example civet and castoreum. Typical synthetic fragrance compounds are products of the ester, ether, aldehyde, ketone, alcohol and hydro-carbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, chamomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise one or more of the following ingredients: astringent active ingredients, oil components, nonionic emulsifiers, coemulsifiers, bodying agents, auxiliaries, for example thickeners or complexing agents, and/or nonaqueous solvents, for example ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be anti-inflammatory, skin-protective or perfumed ethereal oils, synthetic skin-protective active ingredients and/or oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, for example xanthan gum, hydroxyethylcellulose, polyvinylpyrrolidone or high molecular weight polyethylene oxides.

Film formers that can be used are described in the following text. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl]-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur tar distillates, salicyclic acid (or in combination with hexachlorophene), undecylenic acid monoethanolamide sulfosuccinate Na salt, Lamepon® UD (protein undecylenic acid condensate), zinc pyrithione, aluminum pyrithione and magnesium pyrithione/dipyrithione magnesium sulfate.

The swelling agents for aqueous phases may be montmorillonites, clay mineral substances, Pemulen, and alkyl-modified Carbopol grades (Goodrich).

Suitable insect repellents are N,N-diethyl-m-toluamide, 1,2-pentanediol or ethyl butylacetylaminopropionate.

To improve the flow behavior, hydrotropes, for example ethanol, isopropyl alcohol, or polyols, can be used. Polyols which are suitable here preferably have 2 to 15 carbon atoms and at least two hydroxyl groups. The polyols can also contain further functional groups, in particular amino groups, or be modified with nitrogen. Typical examples are:
  glycerol;
  alkylene glycols, for example, ethylene glycol, diethylene glycol, propylene glycol, butylene glycol, hexylene glycol, and polyethylene glycols with an average molecular weight of from 100 to 1 000 daltons;
  technical-grade oligoglycerol mixtures with a degree of self-condensation of from 1.5 to 10, for example, technical-grade diglycerol mixtures with a diglycerol content of from 40 to 50% by weight;
  methylol compounds, such as trimethylolethane, trimethylolpropane, trimethylol-butane, pentaerythritol and dipentaerythritol;

lower alkyl glucosides, in particular those with 1 to 8 carbon atoms in the alkyl radical, for example methyl and butyl glucoside;

sugar alcohols with 5 to 12 carbon atoms, for example sorbitol or mannitol, sugars with 5 to 12 carbon atoms, for example glucose or sucrose;

amino sugars, for example glucamine;

dialcohol amines, such as diethanolamine or 2-amino-1, 3-propanediol.

Suitable preservatives are, for example, phenoxyethanol, formaldehyde solution, parabenes, pentanediol or sorbic acid, and the other classes of substance listed in Annex 6, Part A and B of the Cosmetics Directive.

Perfume oils which may be used are preferably mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, *angelica*, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (*galbanum*, elemi, benzoin, myrrh, olibanum, opoponax). Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, chamomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evemyl, iraldein gamma, phenylacetic acid, geranyl acetate, benzyl acetate, rose oxide, romilat, irotyl and floramat alone or in mixtures.

Medical Device Coatings, Wound Dressings, and Irrigation

In certain embodiments, the disclosure relates to a medical device comprising a coating comprising an extract or one or more compounds in an extract disclosed herein optionally in combination with another antibiotic. In certain embodiments, the medical device is an ear tube, eye lenses, contact lenses, coronary stent, metal screw, pin, plate, rod, catheter, artificial knee, cardioverter defibrillator, artificial hip, heart pacemaker, breast implant, spine screws, rods, and discs, intra-uterine devices In certain embodiments, the disclosure relates to a wound dressing comprising an extract or one or more compounds in an extract disclosed herein wherein the wound dress comprises an absorbent pad and optionally an adhesive optionally in combination with another antibiotic agent. In certain embodiments, the wound dressing is a foam or compression dressing or a cover dressing such as wraps, gauze and tape.

In certain embodiments, the wound dressing comprises alginate or collagen.

In certain embodiments, the wound dressing a hydrocolloid dressing, e.g., carboxy-methylcellulose and gelatin optionally in a polyurethane foam or film, optionally comprising one or more agents selected from, pectin, polysaccharides, and an adhesive.

In certain embodiments, the wound dressing is a hydrogel. Hydrogels are polymers that contain a high content, e.g., greater than 40, 50, 60, 70, 80, 90, or 95%, of hydroxy and/or carboxyl containing monomers or salts thereof, e.g., vinyl alcohol, acrylic acid, 2-hydroxyethylmethacrylate monomers, which can be co-polymers to provide varying degrees of hydration, e.g., copolymerization with ethylene glycol dimethacrylate. Due to the hydrophilic monomers, the hydrogels typically absorb water to contain greater than 70, 80, 85, 90, 95% water by weight. Contemplated hydrogel dressings include: amorphous hydrogel, which are a free-flowing gel that are typically distributed in tubes, foil packets and spray bottles; an impregnated hydrogel, which are typically saturated onto a gauze pad, nonwoven sponge ropes and/or strips; or a sheet hydrogel which are gel held together by a fiber mesh.

A flow of wound rinse/irrigation solution is applied across an open wound surface to achieve wound hydration, to remove deeper debris, and to assist with the visual examination. In certain embodiments, the disclosure relates to methods of irrigating using a solution comprising an extract or one or more compound in an extract disclosed herein. In certain embodiments, the disclosure relates to a wound rinse comprising an extract or one or more compounds in an extract disclosed herein optionally in combination with normal saline, sterile water, detergent, surfactant, preservatives, or iodine.

In certain embodiments, the disclosure contemplate a kit comprising a container comprising an extract or one or more compounds in an extract discloses herein optionally comprising a second container comprising a solution, normal saline, sterile water, detergent, surfactant, preservatives, iodine, hydrogen peroxide, or sodium hypochlorite or other compounds disclosed herein.

EXAMPLES

Collection of Plant Material.

*Schinus terebinthifolia* Raddi, Anacardiaceae leaves, stems, and fruits were collected in bulk from private lands in DeSoto County, Florida in November of 2013 and 2014 after obtaining permission from the land owner. Procedures from the 2003 WHO Guidelines for good agricultural and collection practices (GACP) for medicinal plants were followed for the collection and identification of bulk and voucher specimens, specifically excluding any populations that may have prior exposure to herbicides. Vouchers were deposited at the Emory University Herbarium (GEO) (Voucher CQ-400, GEO Accession No. 020063) and were identified using the standard Flora for Florida. Plant leaves, stems, and fruits were separated and manually cleaned of soil and contaminants. Plant material was then dried in a desiccating cabinet at low heat. Once dry, plant material was sealed in paper bags and stored at room temperature until further processing.

Extraction and Separation.

Crude methanol extracts of fruits were created by blending a ratio of 1 g dry material: 10 mL MeOH into a slurry in a Waring commercial blender for 5 min and sonicating the material for 20 minutes. Following decantation of the extract, plant material was subjected to two more rounds of sonication followed by filtration. Filtered extracts were combined, concentrated at reduced pressure with rotary evaporators (<40)° C., and lyophilized. The dried extract was resuspended in 1:5 MeOH:$H_2O$ at 1 g:31 mL and underwent sequential liquid-liquid partitioning three times each with an equal volume of hexane, EtOAc, and $H_2O$ saturated n-butanol. The organic partitions were dried over $Na_2SO_4$ and filtered. Each partition was concentrated in vacuo at <40° C. The hexane partition was dissolved and transferred to a tared scintillation vial and dried under forced air to yield 430B. The remaining partitions were suspended in dH2O, shell frozen, lyophilized and stored at −20° C. The EtOAc partition was labeled 430C, the n-butanol 430D, and final remaining aqueous partition 430E.

Fractionation by Flash Chromatography.

Following initial quorum quenching assays, the most active partition, 430D was subjected to fractionation through flash chromatography. Fractionation was performed using a CombiFlash® Rf+ (Teledyne ISCO) flash chromatography system with a RediSep Rf Gold silica column. The dry load column was prepared by binding extract 430D to Celite 545 at a ratio of 1:4. Flash chromatography was performed using a three solvent system of (A) hexane, (B) dichloromethane, and (C) methanol. The gradient began with 100% A for 6 column volumes (CV), then went to 100% B over 12 CV and was held for 18.2 CV. The gradient was then changed to 74.5:25.5 B:C over the course of 3.1 CV. These conditions were held for 6.8 CV, following which the gradient changed to 68.8:31.2 B:C over 0.7 CV and was held at these conditions for 7.5 CV. Finally the gradient was adjusted to 100% over 2.2 CV and held for 14.6 CV. The chromatography was monitored at 254 and 280 nm, as well as via ELSD. Tube volumes were combined to create eight fractions: 430D-F1 (tubes 1-5), 430D-F2 (tubes 6-11), 430D-F3 (tubes 12-16), 430D-F4 (tubes 17-24), 430D-F5 (tube 24), 430D-F6 (tubes 25-28), 430D-F7 (tubes 29-31), 430D-F8 (tubes 32-38).

HPLC Characterization of Extracts.

Extracts 430, 430D, and 430D-F5 were characterized by high performance liquid chromatography (HPLC). An Agilent Eclipse XDB-C18 4.6×250 mm, 5-μm analytical column, with a compatible guard column, was used at 40° C. Active sub-fractions were dissolved in DMSO (10 mg mL-1), filtered at 0.2-microns, and a 10 μL injection was eluted at a flow rate of 1.9 mL min-1 using a gradient system consisting of (A) 0.1% formic acid in $H_2O$; (B) 0.1% formic acid in acetonitrile (ACN). The mobile phase was 98:2 A:B at time 0 min, 70:30 A:B at 40 min, 2:98 A:B at 63 min, followed by a hold at 2:98 A:B for 5 min, and ending with a column flush at initial conditions for 5 min. The chromatography was monitored at 217, 254, 320, and 500 nm.

Characterization of 430D-F5 by LC-FTMS.

Liquid chromatography-Fourier transform mass spectrometry (LC-FTMS) was performed on bioactive fractions using a Thermo Scientific LTQ-FT Ultra MS equipped with a Shimadzu SIL-ACHT and Dionex 3600SD HPLC pump. For chromatography an Agilent Eclipse XDB-C18 4.6×250 mm, 5 μm analytical column, with guard column, was used at room temperature. Samples were prepared as previously described and a 50 μL injection was eluted at a flow rate of 1.9 mL min-1 using mobile phases of (A) 0.1% formic acid in $H_2O$; (B) 0.1% formic acid in ACN. The linear gradient had initial conditions of 95:5 A:B at 0 min and held until 3 min, 68:32 A:B at 23 min, 40:55 A:B at 40 min, 0:100 A:B at 75 min and held for 9 min before returning to initial conditions for a 9 min flush. Data was acquired in MS1 mode scanning from a m/z of 150-1500 in negative and positive ESI (electrospray ionization) mode and processed with Thermo Scientific Xcalibur 2.2 SP1.48 (San Jose, CA). The capillary temperature was 275.0° C., sheath gas of 40, source voltage 5.00 kV, source current 100.0 μA, and the capillary voltage −19.0 V or +32.0 V for negative and positive modes, respectively.

Putative formulas were determined by performing isotope abundance analysis on the high-resolution mass spectral data with Xcaliber software and reporting the best fitting empirical formula. Database searches were performed using the Dictionary of Natural Products (Taylor & Francis Group) and Scifinder (American Chemical Society). The databases were reviewed for compounds identified from the genus *Schinus* with molecular masses corresponding to the LC-FTMS data. Any matches were investigated by comparing the literature and the experimental data; putative compound assignments were made when matches were identified.

Extract 430D-F5 Quenches Quorum Sensing and Toxin Production.

Figure 2A:
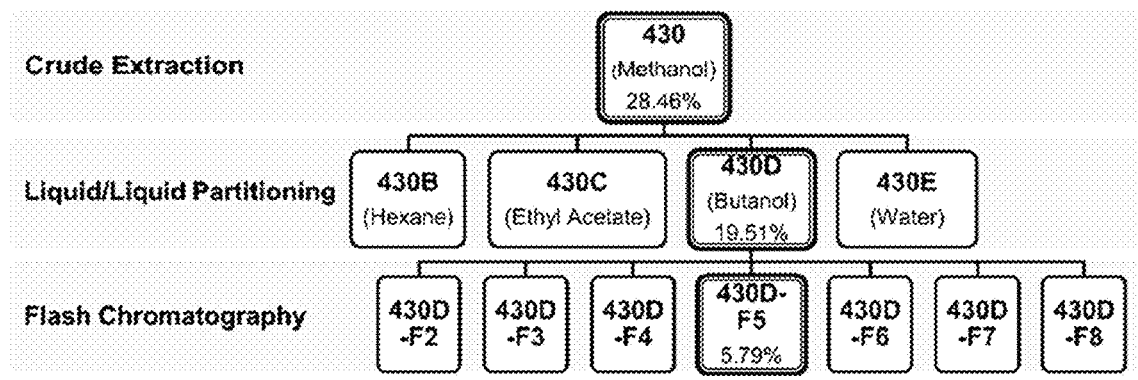
FIG. 2A shows a description of extracts and fractionation scheme for fruits (430 series). Fruits of *Schinus terebinthifolia* were harvested at maturity from wild populations in DeSoto County, Florida. Percent yield from dry plant material is shown for each extract and fraction. The bioassay-guided fractionation scheme is illustrated, demonstrating the path from crude fruit extract to refined bioactive fraction 430D-F5. Percent yields of extracts in relation to starting dry plant material are represented at each separation step. The most active fractions at each step are highlighted in bold.
Figure 2B:
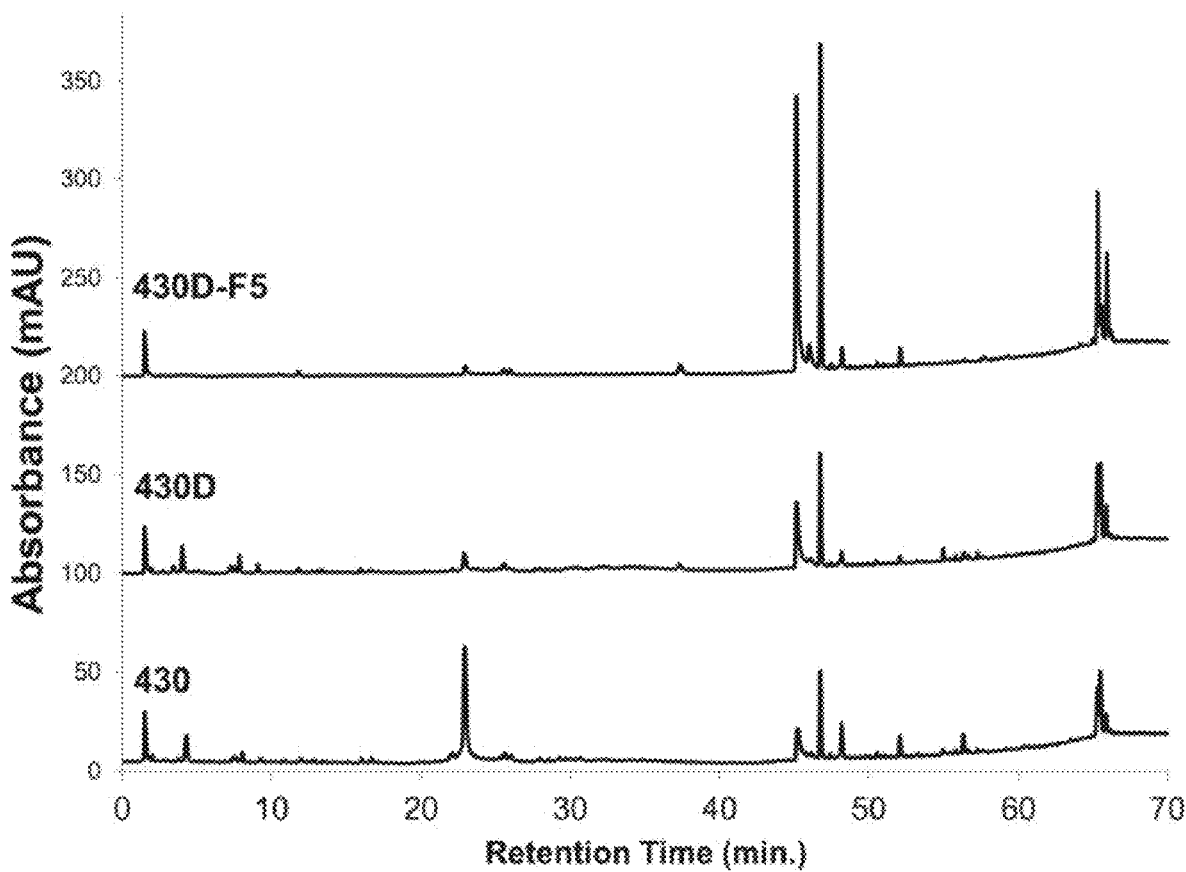
FIG. 2B shows the corresponding HPLC chromatograms for the most active fractions which demonstrate an increase in relative abundance of peaks at a retention time range of 45-50 min.
Figures 3A, 3B:
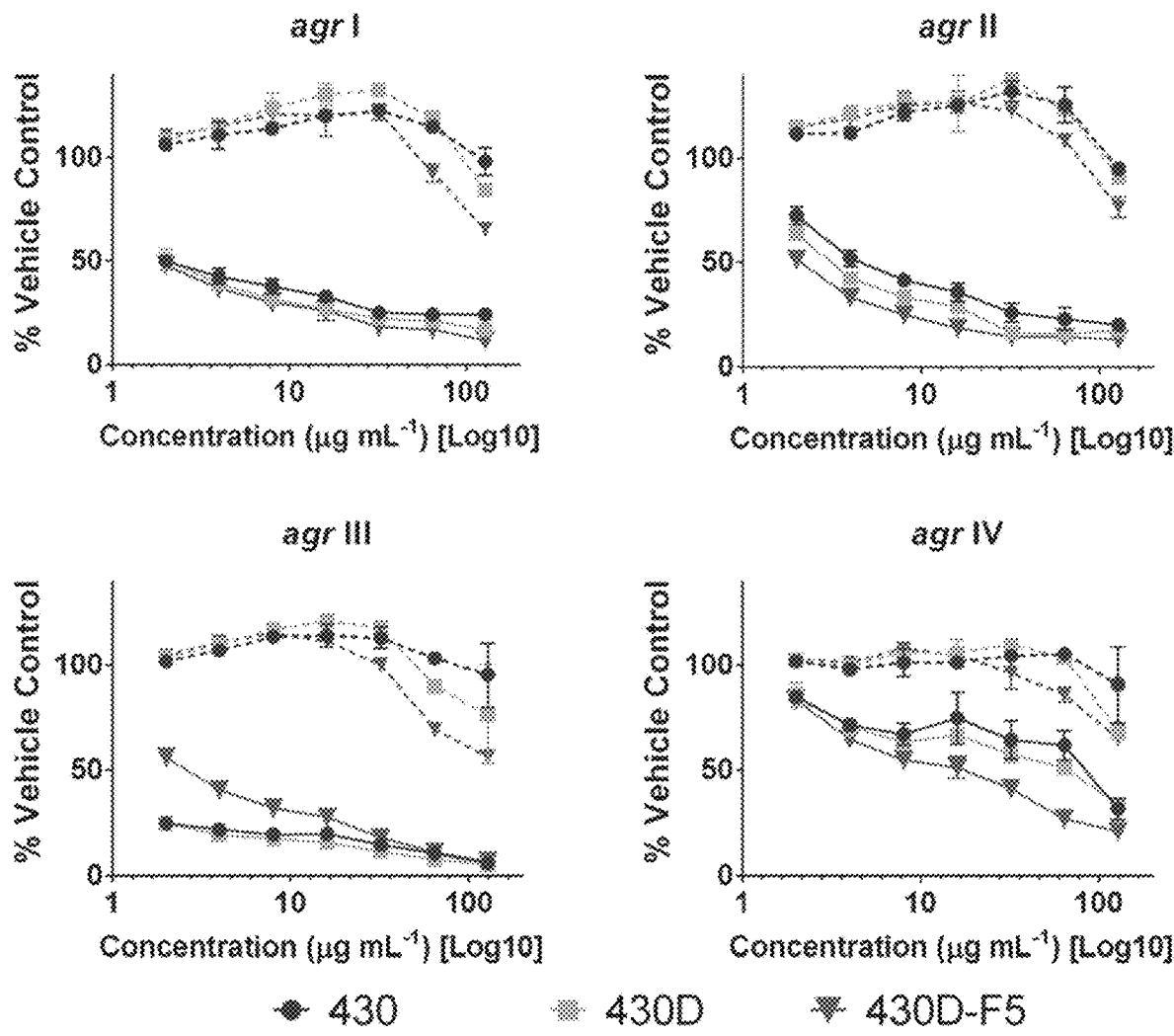
FIG. 3A shows data indicating 430D-F5 inhibits agr activity for all four alleles in a non-biocide manner. Data are represented as percent agr activity or growth of the vehicle (DMSO) control at 24 hours. The solid lines represent agr activity, measured by fluorescence, and the dashed lines represent growth, measured using OD600.
FIG. 3B shows a table of $MIC_{50}$ and $MIC_{90}$ data for each agr allele.

To refine the most active fraction and identify chemical entity inhibitors of *S. aureus* quorum sensing, a bioassay-guided fractionation strategy was employed (FIG. 2A) using agr-fluorescent reporter stains that represent each of the four known agr allelic groups. Strains were grown in the presence of extracts and monitored for growth inhibition by optical density and agr activity by fluorescence. Extract 430D-F5 inhibited agr at sub-inhibitory concentrations for growth in agr I-IV (FIGS. 3A and 3B). An upper limit of 512 μg mL$^{-1}$ was used in growth inhibition assays. An upper limit of 128 μg mL$^{-1}$ was used for detecting anti-agr activity, and $IC_{50}$ values were 2, 4, 4, and 32 μg mL$^{-1}$ for agr I-IV, respectively. An $IC_{90}$ value could only be detected for agr III and was found to be 128 μg mL$^{-1}$.

Figure 4:
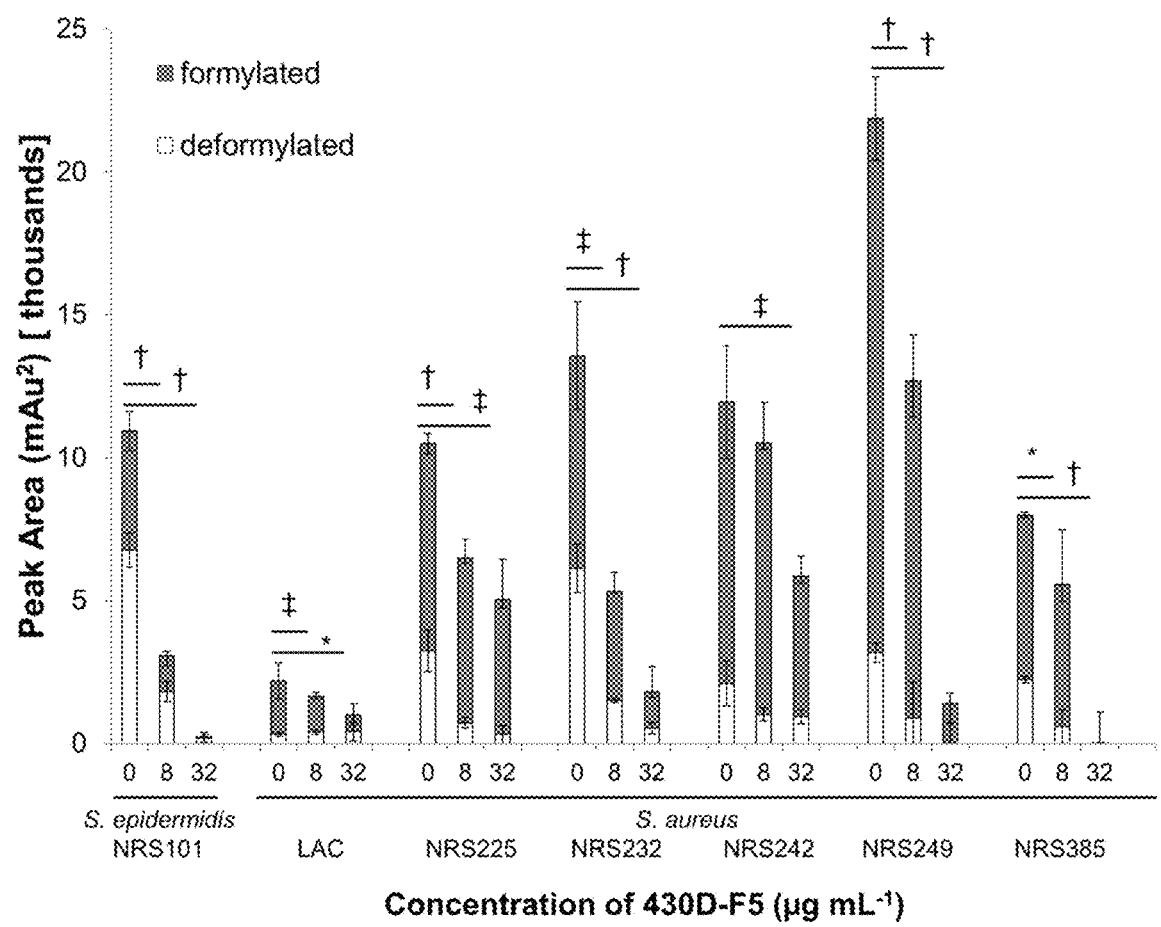
FIG. 4 shows data indicating 430D-F5 inhibits δ-toxin and α-hemolysin production a dose-dependent manner. Levels of δ-toxin were quantified by HPLC analysis of culture supernatant following treatment with sub-MIC50 concentrations of 430D-F5. *S. epidermidis* strain is NRS101, all others *S. aureus*. Results are expressed as the peak area, normalized for optical density (600 nm) at the time of supernatant harvest.

To further confirm the quorum-quenching effects of 430D-F5, a number of in vitro tests were pursued to assess its impact on the translational products of agr. Levels of δ-toxin, a phenol soluble modulin responsible for various pathophysiologic effects including cytolysis of red blood cells, neutrophils and triggering inflammatory responses were quantified by RP-HPLC of the bacterial supernatant following treatment with 430D-F5 at sub-inhibitory concentrations for growth effects. 430D-F5 was significantly effective in reducing δ-toxin production in *S. epidermidis* and in six out of eight *S. aureus* strains examined (FIG. 4A).

Levels of hemolytic α-hemolysin were also assessed via Western blot following co-incubation with 430D-F5 and similarly demonstrated a dose-dependent reduction. Likewise, hemolytic activity declined with 430D-F5 treatment.

Figure 5:
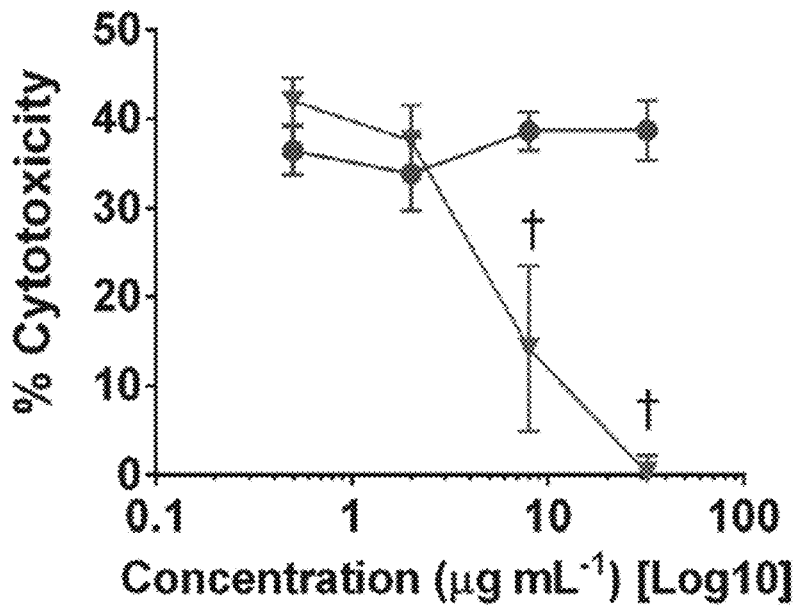
FIG. 5 shows data indicating toxicity of *S. aureus* supernatants to HaCaTs. An immortalized line of human keratinocytes was treated with supernatants of *S. aureus* (NRS385) that was grown +/−430D-F5 or vehicle (DMSO). LDH assay demonstrates that treated cultures lacked the suite of exotoxins in their supernatants, and thus did not impact HaCaT viability.

Lastly, to assess any remaining virulence factors linked to cytotoxicity (e.g., phenol soluble modulins), sterile filtered supernatants of NRS385 cultures (a virulent USA500 isolate) grown with 430D-F5 were exposed to an immortalized line of human keratinocytes and assessed for damage by LDH assay and fluorescent microscopy. HaCaTs were protected from damage by supernatants treated at concentrations as low as 10 μg mL−1, and this was confirmed by fluorescent microscopy and LDH assay (FIG. 5).

430D-F5 Shows Limited Potential for Impact on Skin Microbiome.

To determine its potential of for disrupting the skin microbiome and possibly causing dysbiosis, 430D-F5 was examined for growth inhibitory effects against a panel of common nine skin commensals. With the exception of *Propionibacterium acnes* ($MIC_{50}$ of 16 μg mL$^{-1}$), commensal growth was unaffected at the concentration range necessary for agr-inhibition in *S. aureus* ($IC_{50}$ of 2-32 μg mL$^{-1}$), suggesting that disruption of the skin microbiome would be unlikely.

430D-F5 Impacts Biofilm Formation.

Assessment of the impact of 430D-F5 on biofilm formation revealed a slight significant increase in biofilm production at concentrations ranging from 2-16 μg mL$^{-1}$, but a notable switch in significant reduction of biofilm formation occurred at higher concentrations tested (32-256 μg mL$^{-1}$), also accompanied by a significant increase in planktonic cells at the highest concentrations tested (128-256 μg mL$^{-1}$) (FIG. 6).

430D-F5 is well tolerated by human cells and mouse skin. To determine its potential for toxicity to human cells, the refined fraction (430D-F5) was tested against an immortalized line of human keratinocytes (HaCaT) cells using an LDH assay for cytotoxicity. The IC50 was determined to be 128 μg mL$^{-1}$, which yields an initial therapeutic index (TI) of 64 for agr I, 32 for agr II and III, and 4 for agr IV. Furthermore, when administered intradermally to mouse skin, no skin effects, morbidity or mortality were noted.

430D-F5 Abates Quorum Sensing and Dermonecrosis In Vivo.

Figure 7A:
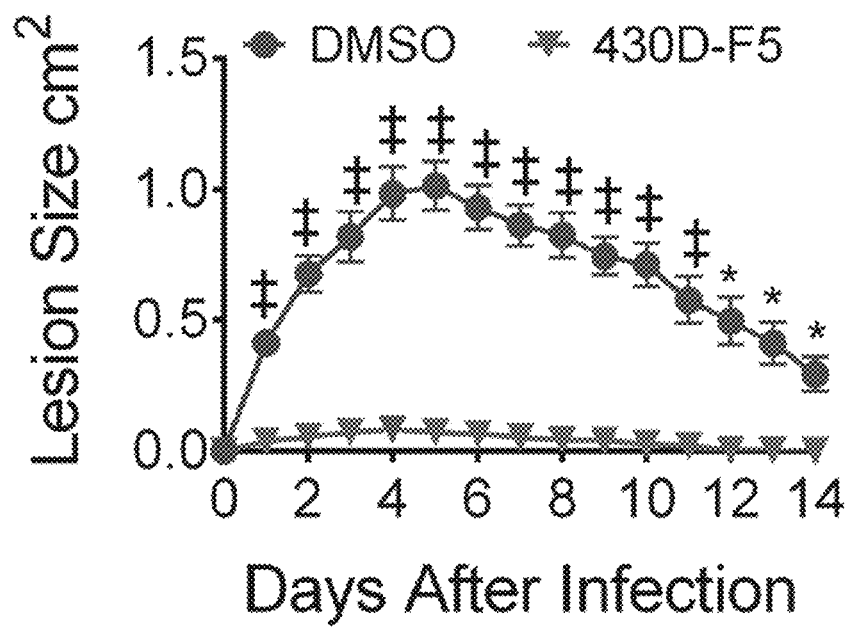
FIG. 7A shows data indicating 430D-F5 attenuates MRSA-induced dermatopathology in a murine model of skin and soft tissue infection. BALB/c mice were intradermally injected with 1×108 CFUs of LAC (USA 300 isolate, AH1263). Mice received a single dose of 430D-F5 (at 50 µg) or the vehicle control (DMSO) at the time of infection. 430D-F5 attenuates dermatopathology with a single dose of 50 µg.
Figure 7B:
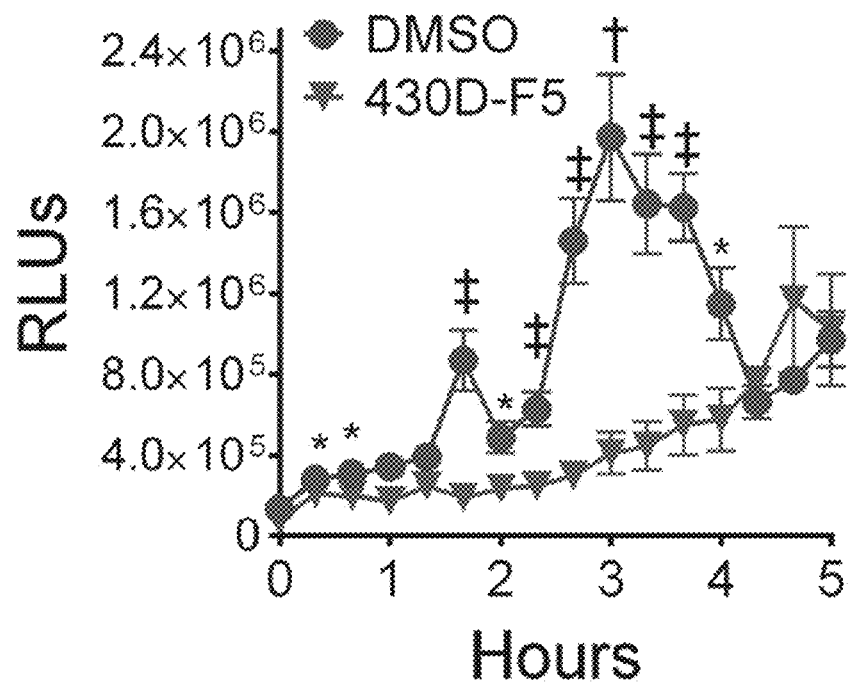
FIG. 7B shows data indicating 430D-F5 mediates quorum quenching in vivo. To determine if 430D-F5 inhibits quorum sensing in vivo, mice were challenged intradermally with an agr P3-lux reporter strain (AH2759)+/−430D-F5 and agr-driven bioluminescence was measured at the indicated time points via IVIS imaging. Quorum sensing peaks at 3 hours post injection, and a single injection of 430D-F5 exhibits significantly significant inhibition of the system for the first 4 h post-injection.

The potent inhibitory activity of 430D-F5 upon agr reporter activity in vitro encouraged us to assess the efficacy of the mixture within the context of MRSA infection in vivo. Using a cutaneous challenge mouse model of USA300 MRSA27, a single dose of 430D-F5 delivered at the time of infection was found to attenuate skin ulcer formation in a dose-dependent manner (FIG. 7A). In addition, 430D-F5 treated animals exhibited significantly less infection-induced morbidity, as assessed by weight loss when compared to vehicle treated controls.

While 430D-F5 mixture clearly attenuated MRSA disease pathology, whether quorum-sensing was inhibited during the course of infection was unclear. To address this question, a MRSA agr P3-lux reporter was tested that could track agr function in real time. Following infectious challenge, the attenuation of MRSA virulence in 430D-F5 treated animals occurred alongside significant suppression of agr activity in vivo (FIG. 7C). Together these data demonstrate that the 430D-F5 mediated attenuation of MRSA pathogenesis corresponds with potent quorum quenching activity both in vitro and in vivo.

Chemical Characterization of 430D-F5.

Figure 8A:
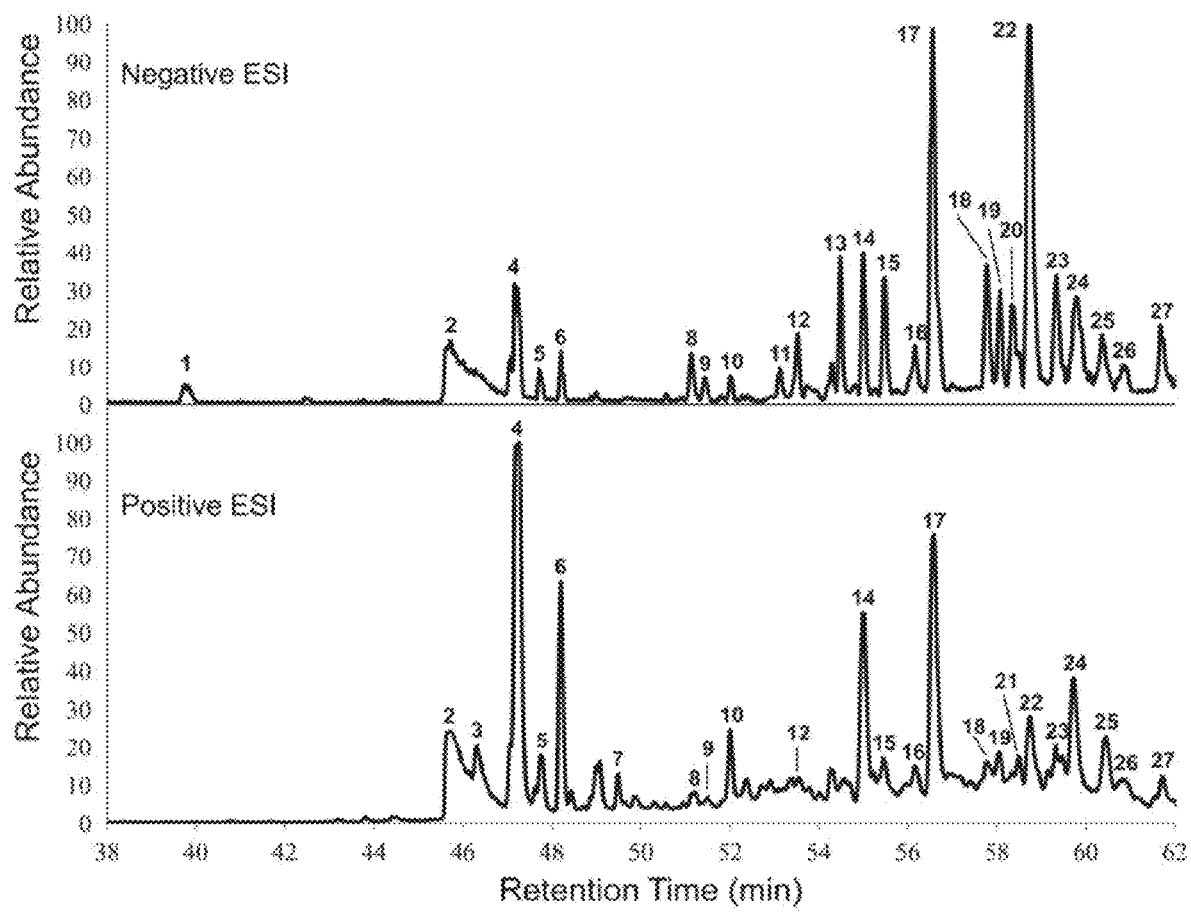
FIG. 8A shows HPLC-DAD chromatogram of 430D-F5 and MS (ESI) positive ion mode and negative ion mode.
Figure 8E:
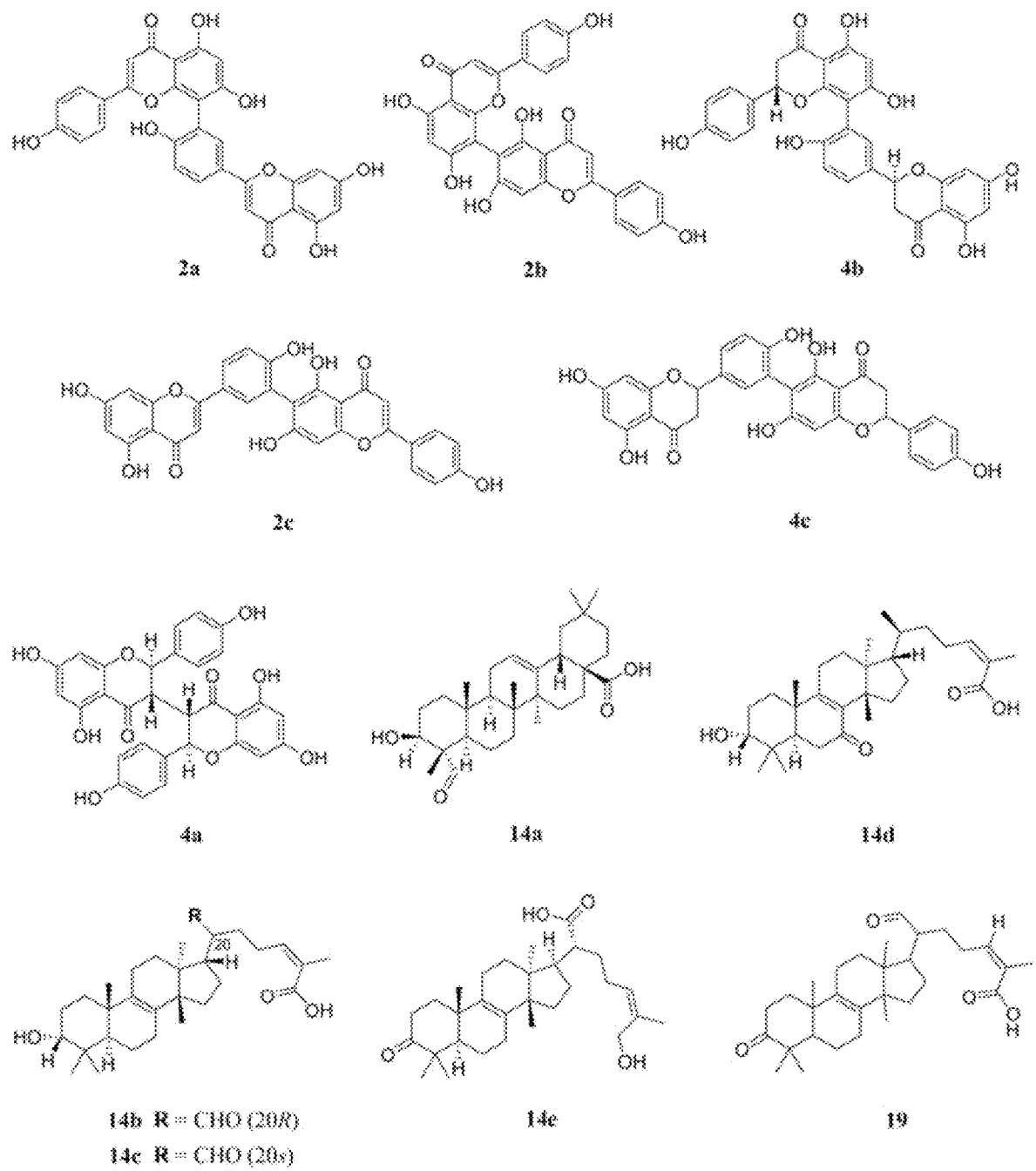
FIG. 8E shows some putative structures of compounds found in 430D-F5. Compounds are listed by peak number, corresponding to the tables in FIG. 8B. Peak 2 was determined to be $C_{30}H_{17}O_{10}$ and putative structural matches include: (2a) amentoflavone, (2b) agathisflavone, and (2c) robustaflavone. Peak 4 was determined to be $C_{30}H_{21}O_{10}$ and putative structural matches include: (4a) chamaejasmin, (4b) tetrahydroamentoflavone, and (4c) tetrahydrorobustaflavone. Peak 14 was determined to be $C_{30}H_{45}O_4$ and putative structural matches include: (14a) albsapogenin, (14b) (13α, 14β, 17α,20R,24Z)-3α-hydroxy-21-oxolanosta-8,24-dien-26-oic acid, (14c) (13α, 14β, 17α,20S,24Z)-3α-hydroxy-21-oxolanosta-8,24-dien-26-oic acid, (14d) (3α, 13α, 14β, 17a,24Z)-3-hydroxy-7-oxo-lanosta-8,24-dien-26-oic acid, and (14e) mollinoic acid. Peak 19 was determined to be $C_{30}H_{45}O_4$ and putative structural matches include (19) iso-masticadienonalic acid.
Figure 9A:
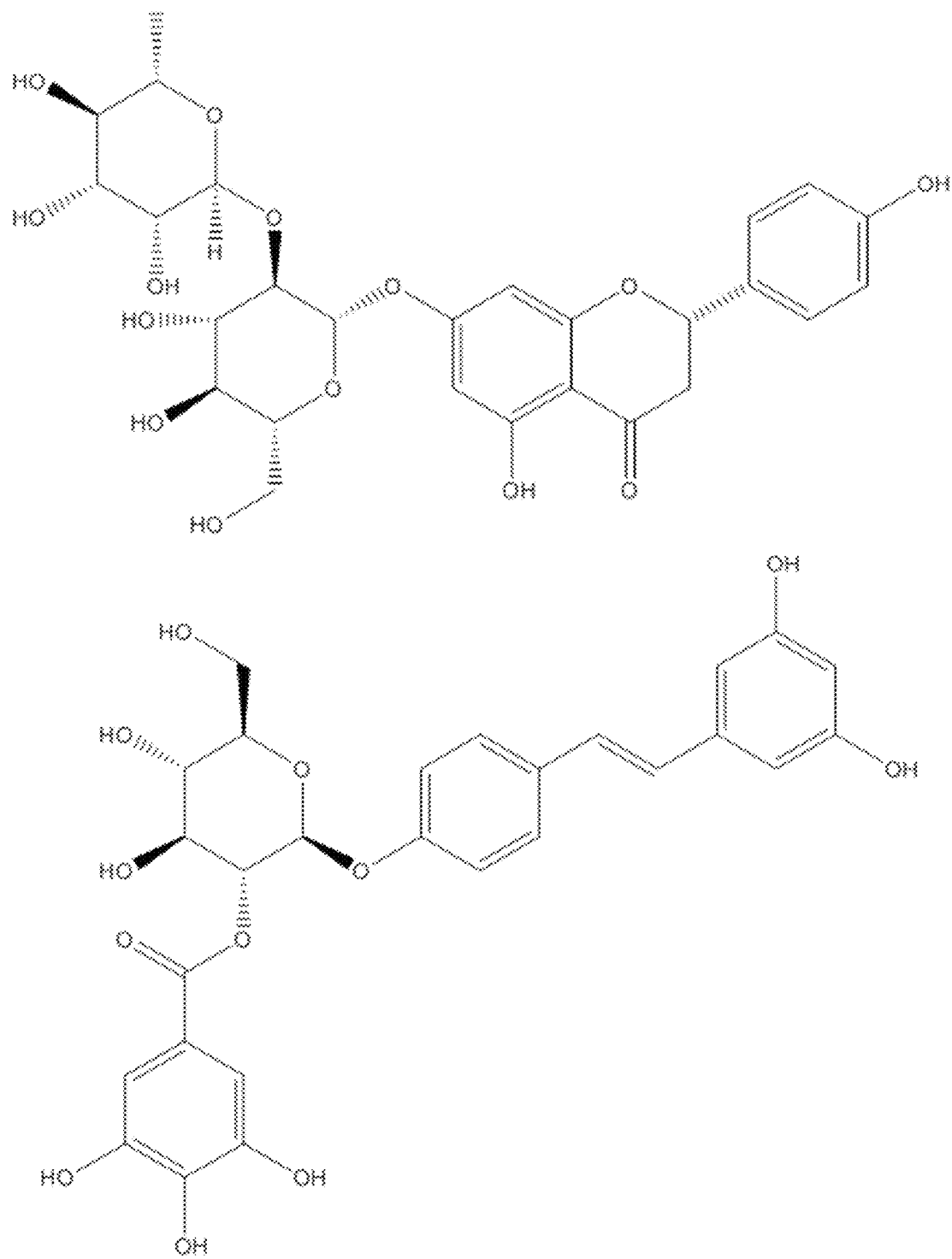
FIG. 9A shows additional putative compounds.
Figure 9B:
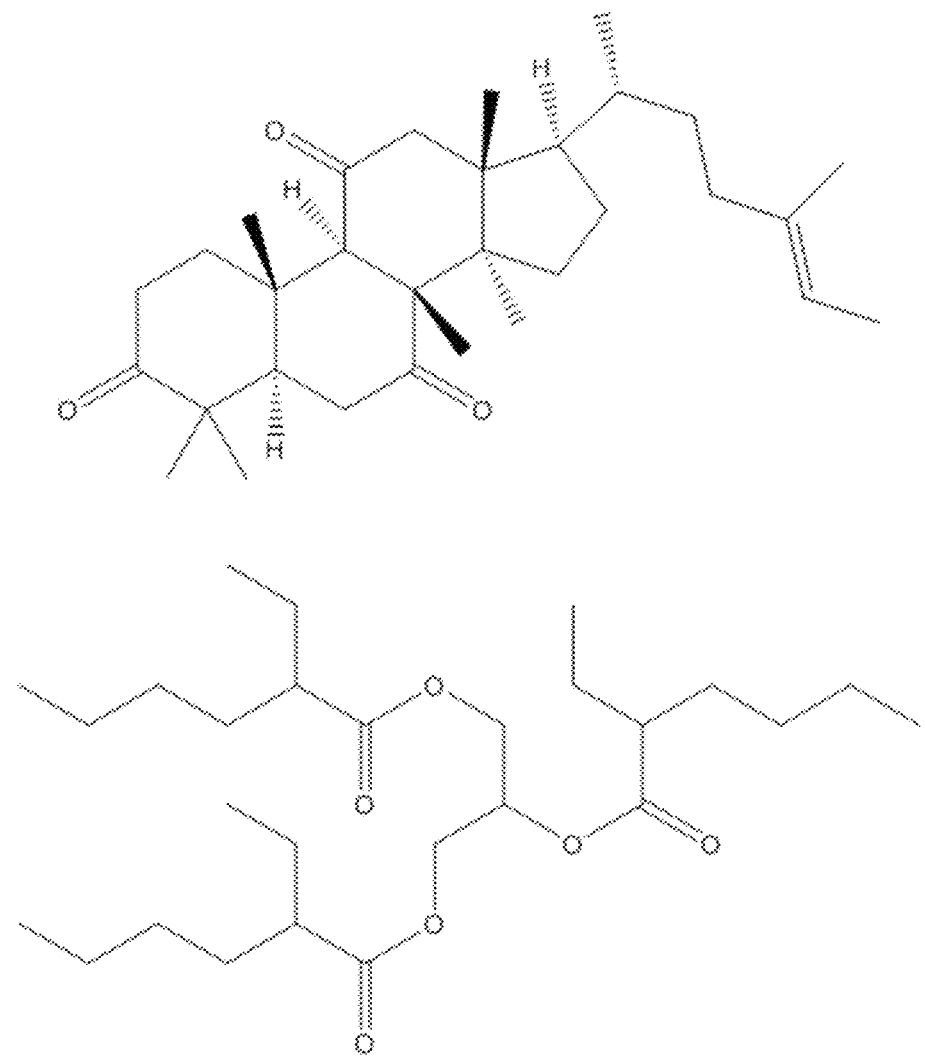
FIG. 9B shows additional putative compounds.
Figure 9C:
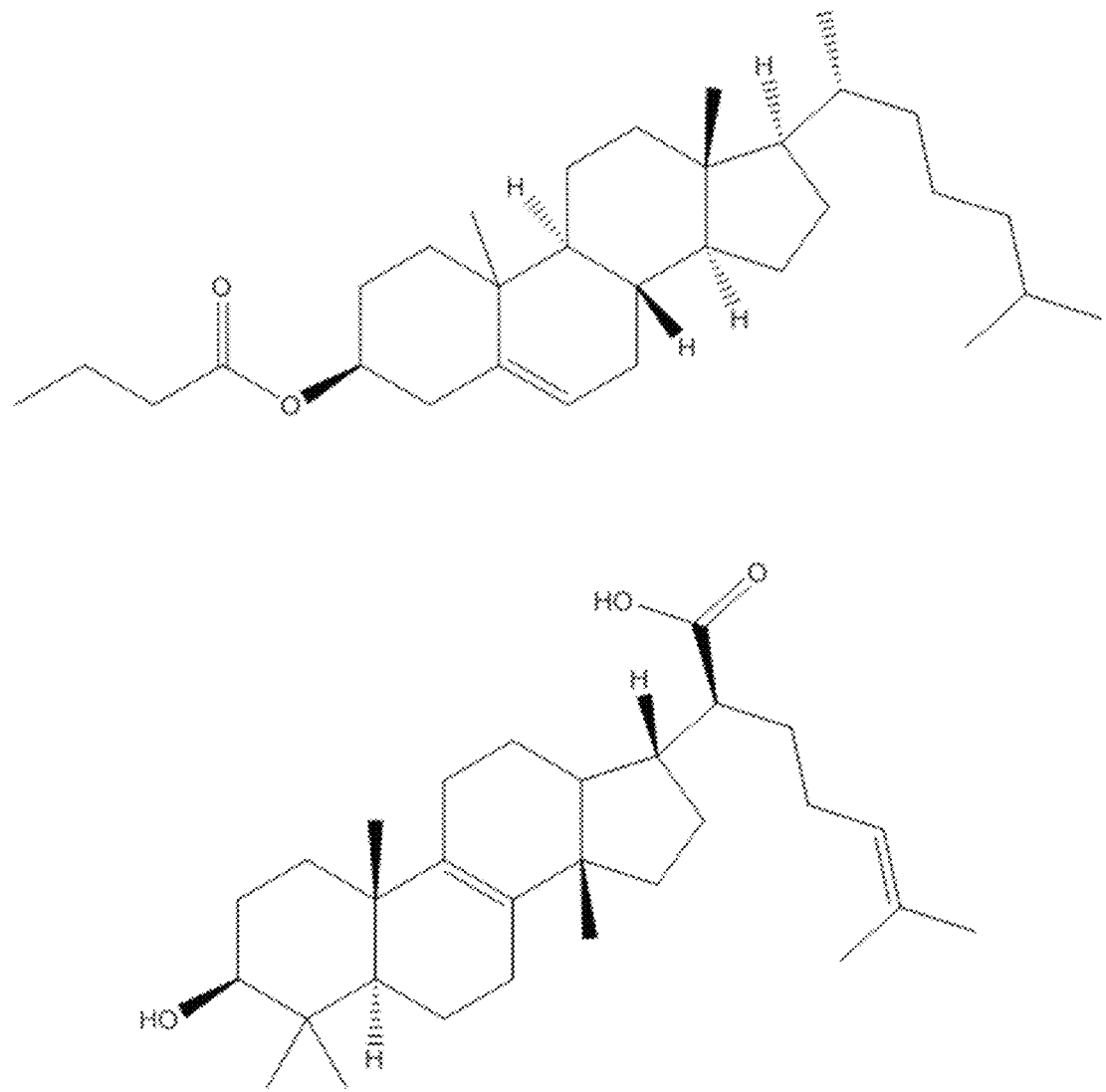
FIG. 9C shows additional putative compounds.
Figure 9D:
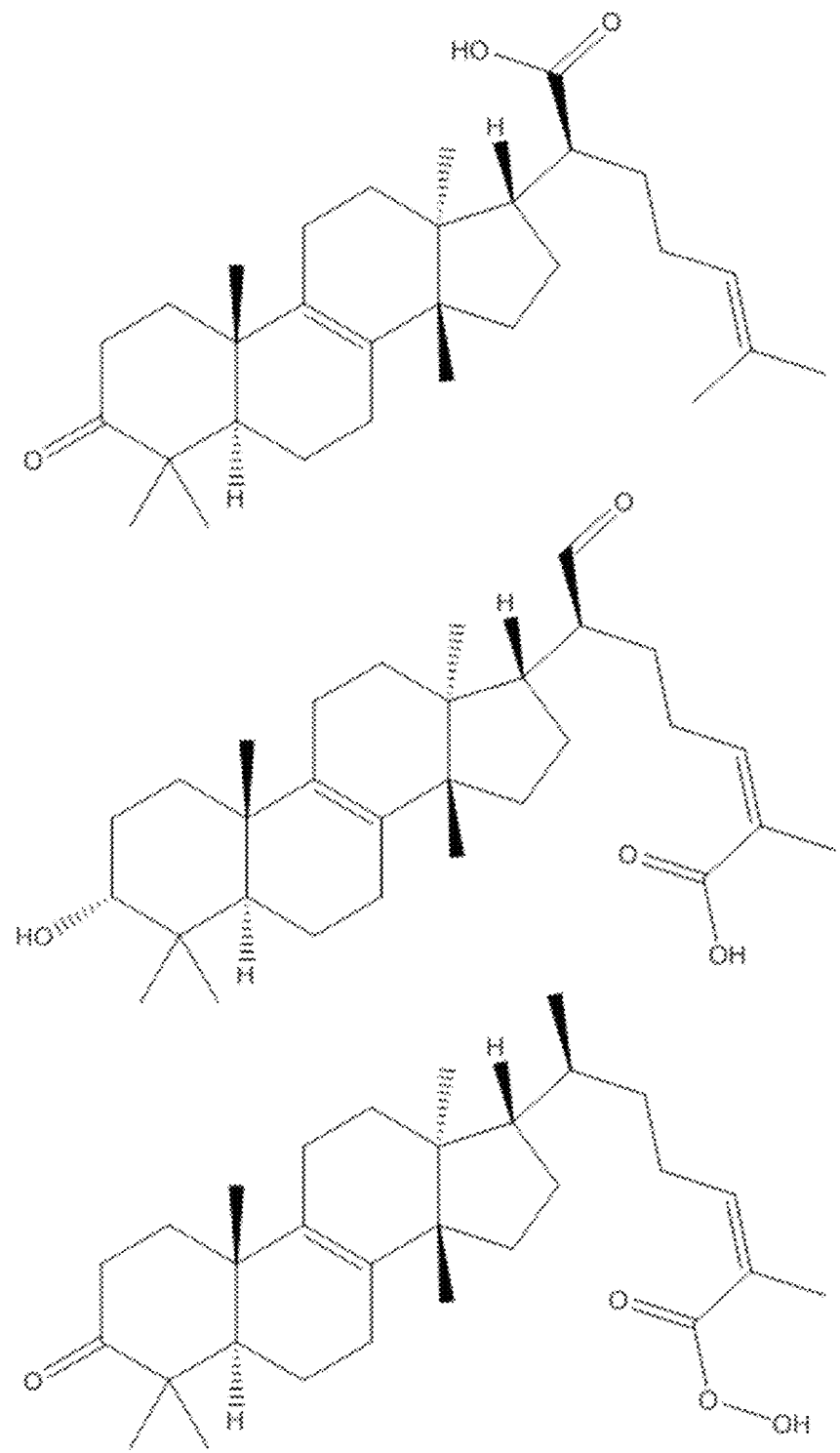
FIG. 9D shows additional putative compounds.
Figure 9E:
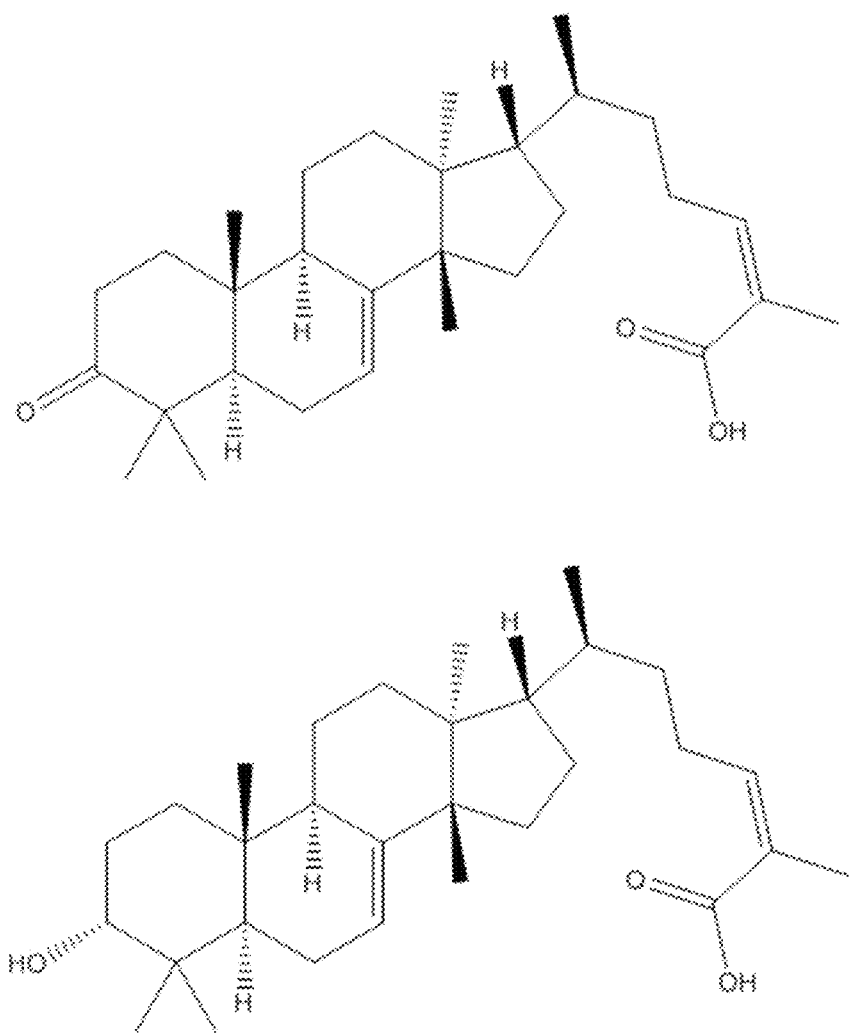
FIG. 9E shows additional putative compounds.
Figure 9F:
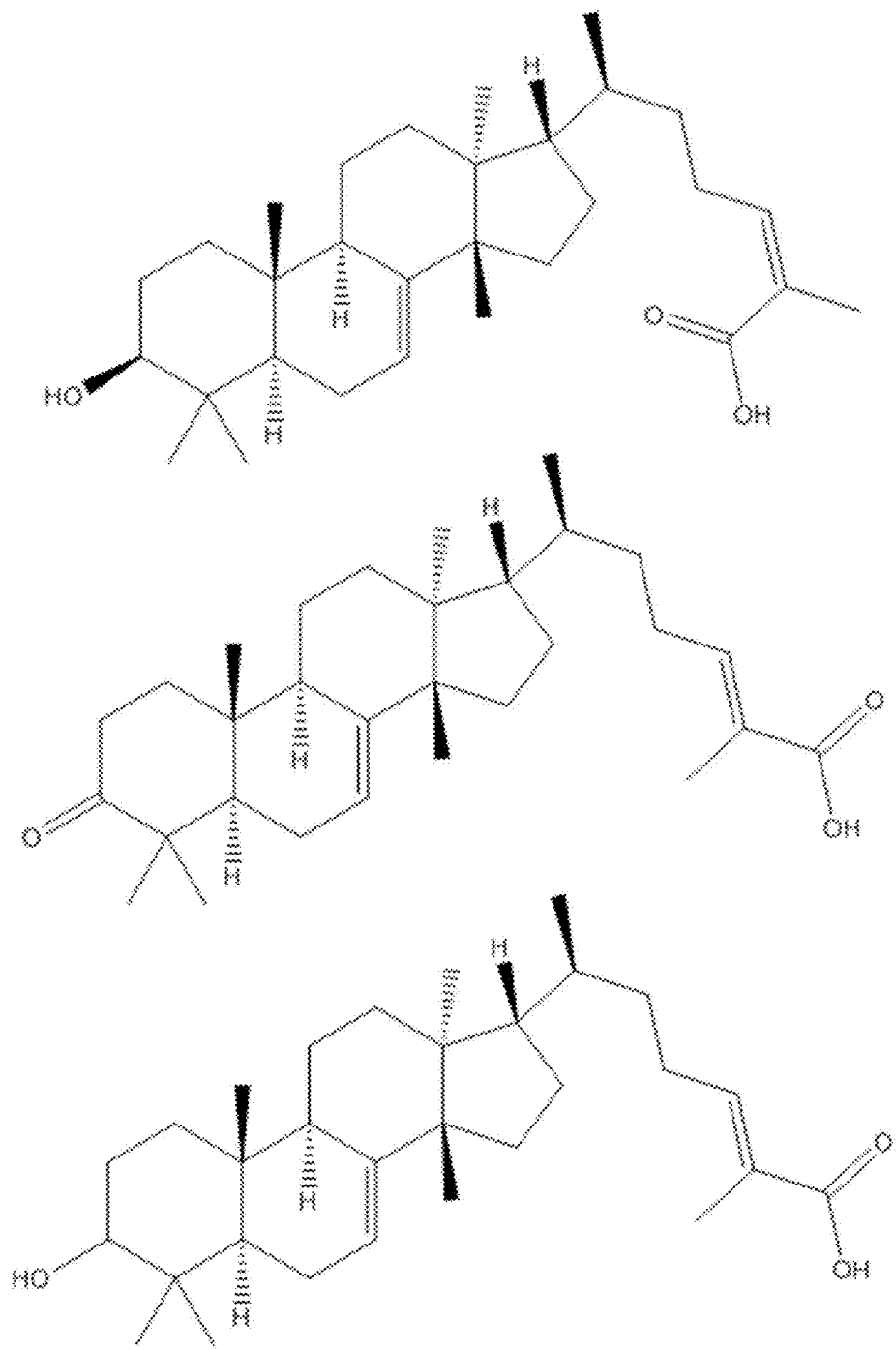
FIG. 9F shows additional putative compounds.
Figure 9G:
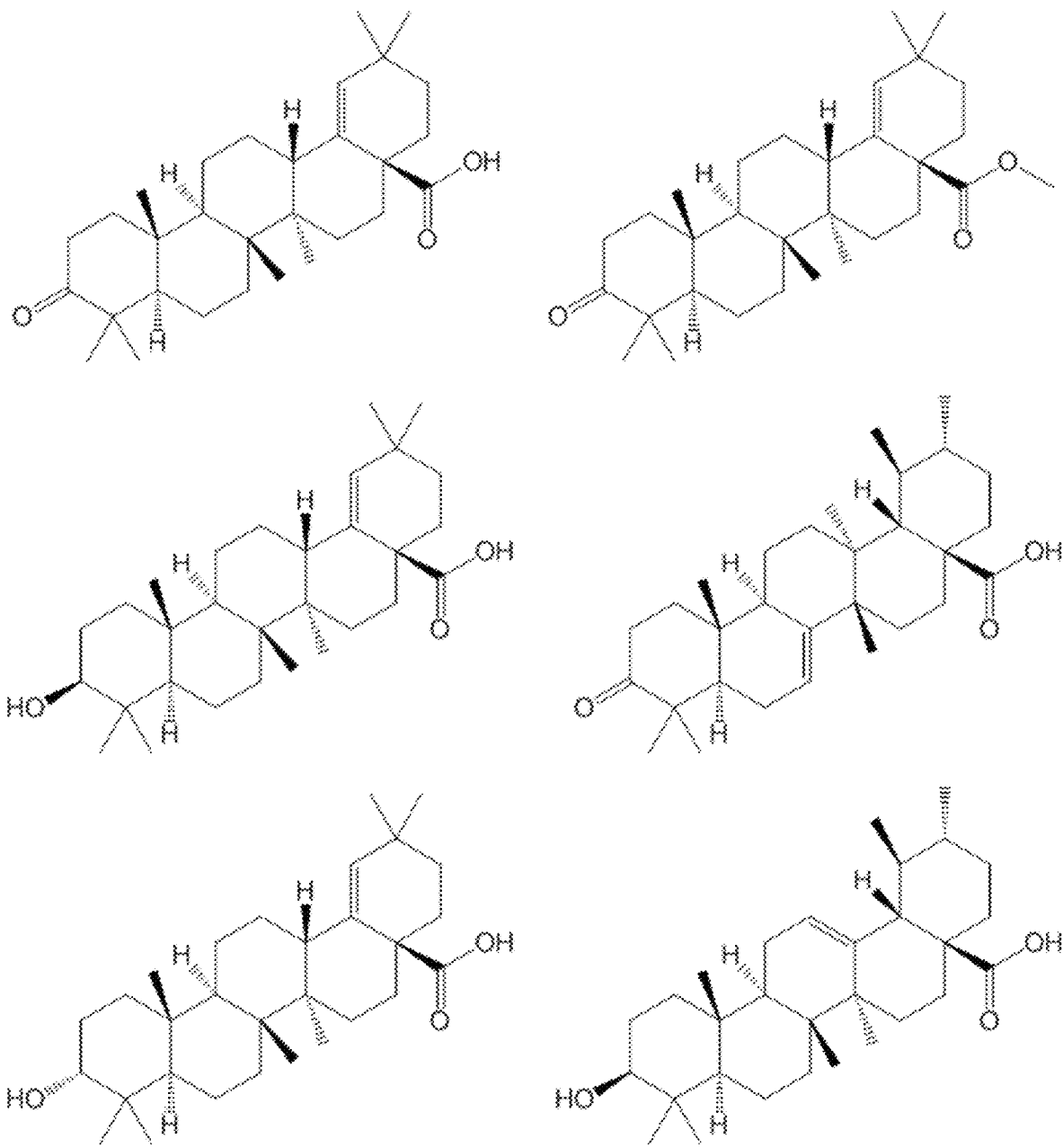
FIG. 9G shows additional putative compounds.
Figure 10A:
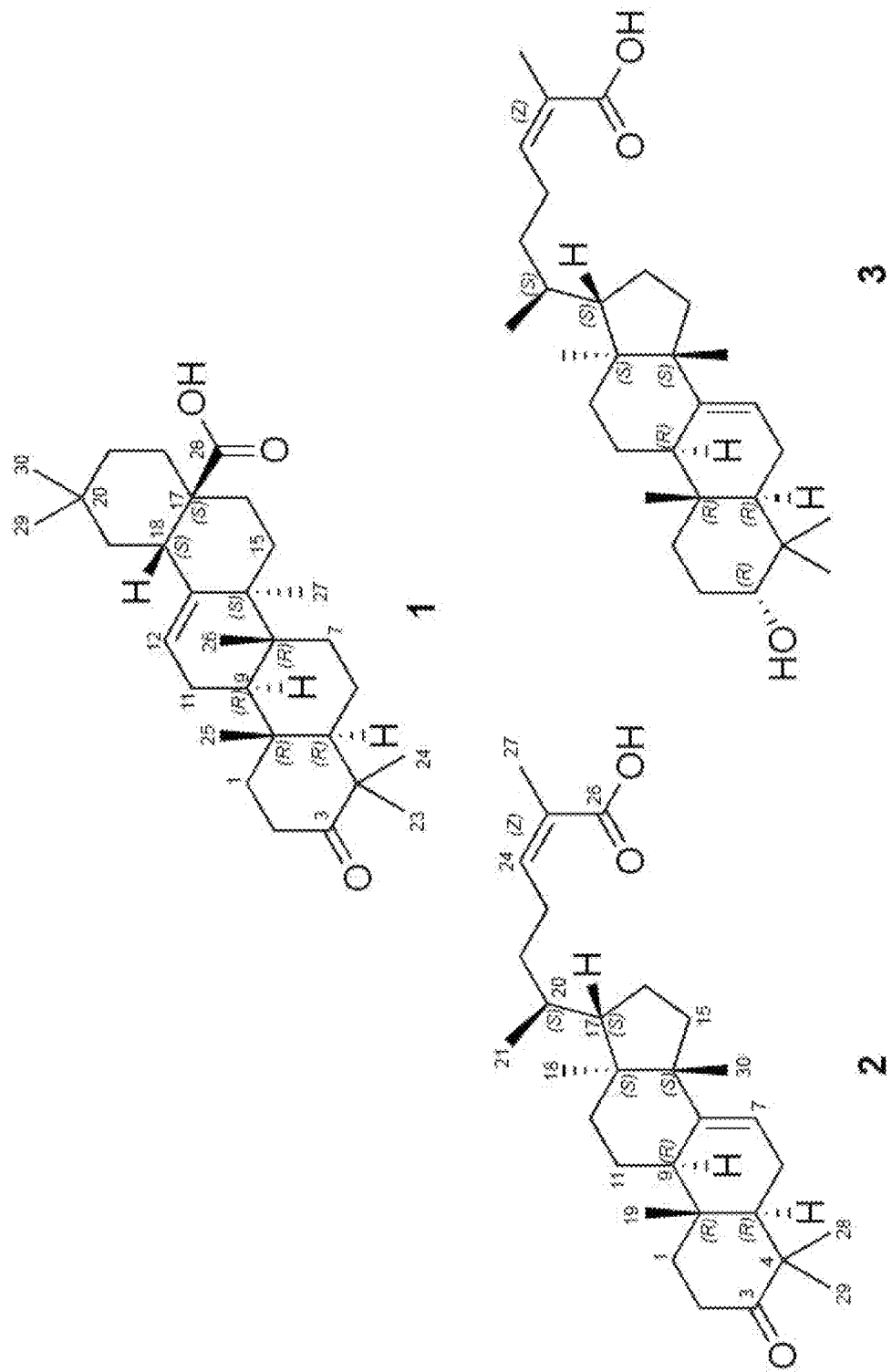
FIG. 10A illustrates embodiments of this disclosure (compounds 1-3).
Figure 10B:
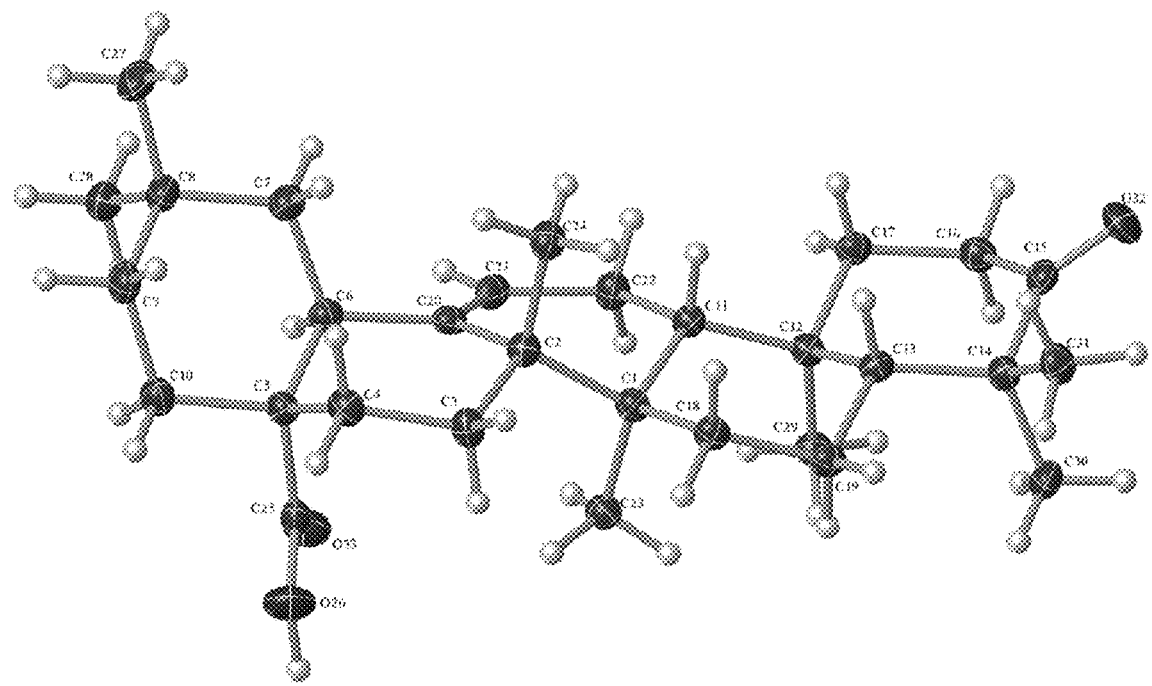
FIG. 10B shows a crystal structure of compound 1.
Figure 10C:
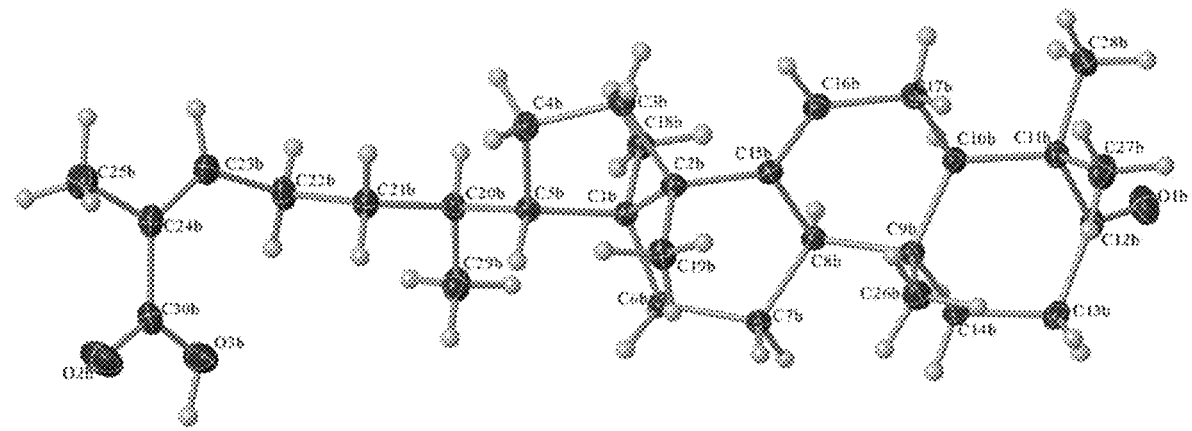
FIG. 10C shows a crystal structure of compound 2.
Figure 10D:
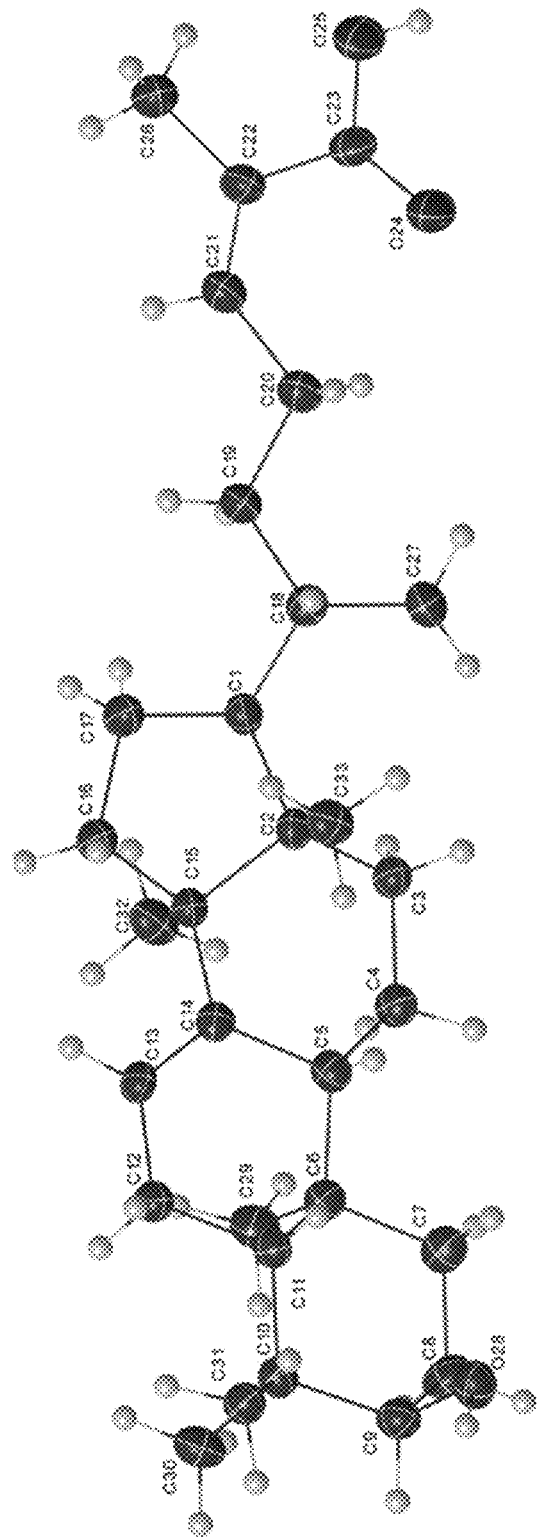
FIG. 10D shows a crystal structure of compound 3.

LC-FTMS analysis of 430D-F5 yielded 27 peaks (FIG. 8A) with exact masses reported in FIGS. 8B, 8C, and 8D. Notably, the 430D-F5 fraction is rich in flavones and steroidal sapogenins (FIG. 8E), exhibiting a different chemical profile than that recently identified in a similar analysis of the quorum quenching activity of a chestnut leaf extract, which was rich in oleanene and ursene derivatives reported in Quave et al. *Castanea sativa* (European Chestnut) leaf extracts rich in ursene and oleanene derivatives block *Staphylococcus aureus* virulence and pathogenesis without detectable resistance. PLOS ONE 10, e0136486, (2015). Peaks 2 and 4 correspond to flavones, representing nearly 34% of the relative abundance in negative ESI mode. Their higher ionization in negative over positive ESI mode supports the conclusion that these are highly hydroxylated flavone skeletons. The steroidal sapogenins correspond to peaks 14 and 19, with 5.3% and 1.0% relative abundance respectively. Their lower abundance could also be due to poor ionization in both positive and negative ESI modes.

Chemical Manipulation of *S. aureus* Virulence Impacts Inflammatory Responses in Atopic Dermatitis (AD) In Vivo Although the pathobiology of AD is not fully understood, it is clear that *S. aureus* plays a major role as it exacerbates inflammation in atopic skin, contributes to dysbiosis of the skin microbiome and promotes skin barrier dysfunction. *S. aureus* virulence is controlled through cell-cell communication systems, or quorum-sensing, regulated by the accessory gene regulator (agr) system. Toxins regulated by agr are responsible for extensive damage to the host tissues, promotion of skin inflammatory cascades and pruritus, and evasion of the immune system response. A growing body of evidence has demonstrated that *S. aureus* virulence can be quenched by organic molecules that interfere with agr. The potential advantages of a chemical approach to suppress virulence rather than kill the pathogen are a lower rate of evolution of resistance and lower collateral killing of protective (commensal) microbial species on the skin. The agr-inhibiting activity of *Schinus terebinthifolia* (Peppertree) is a medicinal plant that has use in traditional medicine. A botanical drug product from this plant source was developed and may be used as a tool to explore how chemical manipulation of *S. aureus* virulence impacts inflammatory responses in AD in vivo.

The refined extract "430D-F5" has demonstrated quorum quenching activity in numerous in vitro models, as well as efficacy in blocking toxin-mediated disease in murine skin abscess models. Bioactive compounds from 430D-F5 were isolated and the structures and pharmacological profiles were determined. These compounds may be use for formulation for optimal topical delivery. Anti-virulence compounds are examined in a vertebrate (mouse) AD model for *S. aureus* driven skin inflammation.

The refined extract "430D-F5" from *Schinus terebinthifolia* inhibits agr at sub-growth inhibitory concentrations. Quorum-quenching phenotype was observed using transcriptional reporters and was conserved across clinical MRSA isolates. Moreover, quenching was demonstrated in vivo through use of a lux reporter; this corresponded to ablation of dermonecrosis and lesion size in a murine skin challenge model. Three bioactive compounds were isolated from 430D-F5. Chemical structures were determined NMR and X-ray crystallography. Compounds with QQ activity in all four agr allelic variants show $EC_{50}$ values ranging from 0.82-8.9 μM.

Isolation of QQ-Compounds from 430D-F5.

The extract was further fractionated by preparative HPLC [Agilent 1260 infinity II LC system (CA, USA) equipped with a UV-vis detector, auto collector, Agilent XDB-C18 (30×250 mm×5 μm) column, eluted with A: H2O, B: MeOH at 42.5 mL/min using the following gradient: 0 min 50% B, 0-11.5 min 50% B, 11.5-36.5 min 100% B, 36.5-46.5 min 100% B, detection at 254 and 320 nm)] to afford 12 sub-fractions. 430D-F5-PF11 (140.0 mg) and 430D-F5-PF12 (231.5 mg) showed the highest activity in QQ assays. These were further fractionated using the same prep-HPLC system described above and eluted with A: H2O, B: Acetonitrile at 42.5 mL/min using the following gradient: 0 min 90% B, 12 min 95% B, 30 min 95% B. From 430D-F5-PF11 were obtained compound 1 (100.0 mg), 2 (17.8 mg) and 3 (21.3 mg). From 430F-F5-PF12 were isolated compound 2 (178.1 mg) and 3 (52 mg).

QQ-Activity of Compounds 1-3.

The QQ and growth-inhibitory activity of the isolated compounds and parent extract (430) was assessed using our reporter assays. The compounds were superior to the extract in agr I-IV, and performed at sub-MIC levels, with the exception of the agr III strain. The $EC_{50}$, which represents the concentration (μM) at which a compound exerts half of its maximal response, was calculated (Table 1), demonstrating that compound 3 is the most potent of the compounds isolated to date across agr I-IV (e.g., EC50 in agr II of 0.824 μM).

| Compound | agr I | agr II | agr III | agr IV |
|---|---|---|---|---|
| 1 | 12.19 | 7.25 | 71.75 | 35.76 |
| 2 | 291.41 | 898.91 | 193.90 | 7.76 |
| 3 | 3.73 | 0.82 | 8.99 | 4.40 |

Structural Elucidation of Compounds 1-3 (FIG. 10).

LC-FTMS was performed on bioactive pure compounds using a Thermo Scientific LTQ-FTMS with a nanospray source. Data was acquired in MS1 mode scanning from a m/z of 150-1500 in negative and positive ESI (electrospray ionization) mode and processed with Thermo Scientific Xcalibur™ 2.2 SP1.48 (San Jose, CA). The capillary temperature was 275.0° C., sheath gas of 40, source voltage 5.00 kV, source current 100.0 μA, and the capillary voltage—19.0 V or +32.0 V for negative and positive modes, respectively. Compounds were determined to be C30H46O3 (1 and 2) and C30H48O3 (3). NMR spectra were measured on a Bruker AVANCE III™ HD 600 (600 MHz for 1H-NMR, 5 mm CryoProbe™) spectrometer in CD3OD or CDCl3 solvents. Chemical shifts (δ) were reported in ppm from residual chloroform (δ: 7.24) or tetramethylsilane (δ: 0.00) as a reference. Compounds 430F-F5-PF11-SF5 (1) and 430F-F5-PF12-SF9 (2) were recrystallized from MeOH by putting into −20° C. refrigerator overnight. A suitable crystal was selected and the crystal was mounted on a Rigaku Xta-LAB™ Synergy-S diffractometer. The crystal was kept at 107(8) K during data collection. Using Olex2™, the structure was solved with the ShelXT structure solution program using Intrinsic Phasing and refined with the ShelXL refinement package using Least Squares minimization.

The invention claimed is:

1. A pharmaceutical formulation comprising:
   (a) a therapeutically effective amount of a compound of the formula below

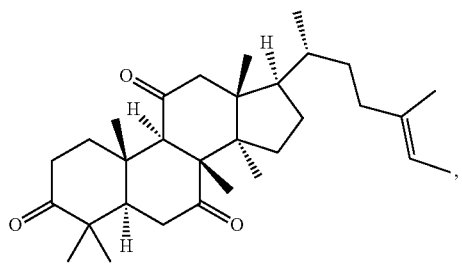 [SMILES: C/C=C(\C)CC[C@@H](C)[C@H]1CC[C@]2(C)[C@]1(C)CC(=O)[C@@H]1[C@@]3(C)CCC(=O)C(C)(C)[C@@H]3CC(=O)[C@]12C]

or a salt thereof, and
   (b) a pharmaceutically acceptable excipient.

2. The pharmaceutical formulation of claim 1, wherein the formulation is a particle, bead, tablet, capsule, or pill.

3. The pharmaceutical formulation of claim 1, wherein the formulation is a lotion, liquid, or gel.

4. The pharmaceutical formulation of claim 1, wherein the formulation further comprises an additional antibiotic.

5. The pharmaceutical formulation of claim 1, wherein the formulation further comprises a steroid.

6. The pharmaceutical formulation of claim 1, wherein the formulation further comprises an anti-inflammatory agent.

7. A method of treating or preventing a bacterial infection in a subject comprising administering to the subject an effective amount of a pharmaceutical formulation comprising:
   (a) a therapeutically effective amount of a compound of the formula below

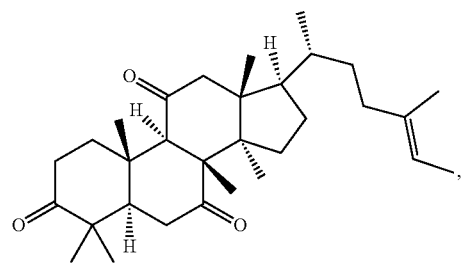 [SMILES: C/C=C(\C)CC[C@@H](C)[C@H]1CC[C@]2(C)[C@]1(C)CC(=O)[C@@H]1[C@@]3(C)CCC(=O)C(C)(C)[C@@H]3CC(=O)[C@]12C]

or a salt thereof, and
   (b) a pharmaceutically acceptable excipient.

8. The method of claim 7, wherein the subject has an abscess, furuncle, cellulitis, folliculitis, atopic dermatitis, psoriasis, impetigo, septic arthritis, brain abscess, burn wound, venous ulcer, diabetic foot ulcer, surgical wound, carbuncle, or meningitis.

9. The method of claim 7, wherein the subject has bacteremia, pneumonia, staphylococcal food poisoning, necrotizing pneumonia, necrotizing fasciitis, scaled skin syndrome, post-operation bacterial infection, medical device bacterial infection, bacterial infection of the skin, soft tissue bacterial infection, or toxic shock syndrome.

10. The method of claim 7, wherein the bacterial infection is a toxin-mediated bacterial infection.

11. The method of claim 10, wherein the toxin-mediated bacterial infection is a *Staphylococcus*-mediated bacterial infection.

12. The method of claim 7, wherein administering comprises topical administration of the formulation.

13. The method of claim 7, further comprising administering to the subject an additional antibiotic.

14. The method of claim 13, wherein the formulation further comprises an additional antibiotic.

15. The method of claim 7, further comprising administering to the subject a steroid.

16. The method of claim 15, wherein the formulation further comprises a steroid.

17. The method of claim 7, further comprising administering to the subject an anti-inflammatory agent.

18. The method of claim 17, wherein the formulation further comprises an anti-inflammatory agent.

* * * * *